United States Patent
Suzuki

(10) Patent No.: US 12,236,531 B2
(45) Date of Patent: Feb. 25, 2025

(54) MENISCUS PROJECTION PLANE SETTING APPARATUS, MENISCUS PROJECTION PLANE SETTING METHOD, AND MENISCUS PROJECTION PLANE SETTING PROGRAM

(71) Applicant: FUJIFILM Corporation, Tokyo (JP)

(72) Inventor: Kenji Suzuki, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 398 days.

(21) Appl. No.: 17/750,382

(22) Filed: May 22, 2022

(65) Prior Publication Data

US 2022/0292779 A1 Sep. 15, 2022

Related U.S. Application Data

(63) Continuation of application No. PCT/JP2020/039629, filed on Oct. 21, 2020.

(30) Foreign Application Priority Data

Dec. 11, 2019 (JP) .................................. 2019-223582

(51) Int. Cl.
*G06T 19/00* (2011.01)
*A61B 6/00* (2024.01)
(Continued)

(52) U.S. Cl.
CPC .............. *G06T 19/00* (2013.01); *A61B 6/505* (2013.01); *A61B 6/5211* (2013.01);
(Continued)

(58) Field of Classification Search
CPC ......... G06T 2207/10088; G06T 7/0012; G06T 2207/30008; G06T 19/00; G06T 2210/41;
(Continued)

(56) References Cited

U.S. PATENT DOCUMENTS

| | | | |
|---|---|---|---|
| 7,745,479 B2 | 6/2010 | Nettekoven et al. | |
| 8,965,088 B2 * | 2/2015 | Tsougarakis | A61B 34/10 606/88 |

(Continued)

FOREIGN PATENT DOCUMENTS

| | | |
|---|---|---|
| JP | 2000139870 | 5/2000 |
| JP | 2006517433 | 7/2006 |

(Continued)

OTHER PUBLICATIONS

Ichiro Sekiya, "Establishment of evaluation criteria for knee cartilage and meniscus using MRI three-dimensional automatic analysis software" with English translation thereof, Business Report on the Evaluation Fundamental Technology Project for the Industrialization of Regenerative Medicine (Development of Evaluation Methods, etc. for the Industrialization of Regenerative Medicine, etc.), Sep. 27, 2017, pp. 1-15.

(Continued)

*Primary Examiner* — Negussie Worku
(74) *Attorney, Agent, or Firm* — JCIPRNET

(57) ABSTRACT

A meniscus projection plane setting apparatus, a meniscus projection plane setting method, and a meniscus projection plane setting program appropriately set a projection plane when generating a projection image of a meniscus from a three-dimensional image including a knee joint. An image acquisition unit acquires the three-dimensional image of the knee joint. A plane setting unit sets a plane that approximates a joint surface of the knee joint as the projection plane for generating the projection image by projecting the meniscus at the knee joint included in the three-dimensional image.

23 Claims, 20 Drawing Sheets

(51) Int. Cl.
*A61B 6/50* (2024.01)
*G06T 7/00* (2017.01)
*G06T 7/11* (2017.01)
*G06T 7/62* (2017.01)

(52) U.S. Cl.
CPC .............. *G06T 7/0012* (2013.01); *G06T 7/11* (2017.01); *G06T 7/62* (2017.01); *G06T 2200/04* (2013.01); *G06T 2207/10088* (2013.01); *G06T 2207/30008* (2013.01); *G06T 2210/41* (2013.01); *G06T 2219/008* (2013.01)

(58) Field of Classification Search
CPC ... G06T 7/11; G06T 7/62; G06T 2207/10081; G06T 2200/04; G06T 2219/008; G06T 7/40; G06T 7/97; G06T 11/00; G06T 15/10; G06T 2207/10104; G06T 2207/30004; G06T 2215/08; G06T 2219/021; G06T 3/067; A61B 5/055; A61B 5/4514; A61B 6/505; A61B 6/5211; A61B 5/0013; A61B 5/0035; A61B 5/107; A61B 5/4528; A61B 5/4585; A61B 5/72; A61B 6/03; A61B 6/032; A61B 6/037; A61B 6/463; A61B 6/5217; A61B 6/5223; A61B 5/004; A61B 17/562; A61B 2562/0219; A61B 5/0031; A61B 5/01; A61B 5/11; A61B 5/112; A61B 5/4851; A61B 5/686; G06V 20/64; G06V 2201/033; A61F 2/38; A61F 2/3859; A61F 2/389; A61F 2/30; A61F 2/30756; A61F 2/3877; A61F 2/4657; A61F 2/488; A61F 2002/2825; A61F 2002/2892; A61F 2002/30131; A61F 2002/30171; A61F 2002/30563; A61F 2002/3067; A61F 2002/30759; A61F 2002/30841; A61F 2002/30845; A61F 2002/3895; A61F 2002/4631; A61F 2002/4666; A61F 2002/4668; A61F 2002/4674
USPC ......................................................... 382/131
See application file for complete search history.

(56) References Cited

U.S. PATENT DOCUMENTS

| | | | |
|---|---|---|---|
| 8,965,108 | B2* | 2/2015 | Chabanas ............... A61B 34/10 382/128 |
| 10,568,580 | B2* | 2/2020 | Morger ................. A61B 5/0033 |
| 10,806,392 | B2 | 10/2020 | Itai |
| 2004/0147927 | A1* | 7/2004 | Tsougarakis ........ A61F 2/30942 623/20.14 |
| 2012/0083377 | A1* | 4/2012 | Huemmer ............. F02N 15/063 475/149 |
| 2013/0071828 | A1* | 3/2013 | Lang ...................... A61B 5/112 434/274 |
| 2014/0066938 | A1* | 3/2014 | Catanzarite .......... A61B 17/157 606/88 |
| 2015/0216615 | A1* | 8/2015 | Tsougarakis ........ A61F 2/30756 703/11 |
| 2018/0035964 | A1* | 2/2018 | Funabasama .......... G16H 50/30 |
| 2018/0070874 | A1* | 3/2018 | Itai ....................... A61B 5/0035 |
| 2018/0365827 | A1* | 12/2018 | Lilliestråle ........... G06V 10/751 |
| 2020/0188026 | A1* | 6/2020 | de Souza ............. A61B 6/5223 |
| 2022/0012890 | A1* | 1/2022 | Wu ....................... G06T 7/0012 |

FOREIGN PATENT DOCUMENTS

| | | |
|---|---|---|
| JP | 2009517433 | 4/2009 |
| JP | 2011095796 | 5/2011 |
| JP | 2013533765 | 8/2013 |
| JP | 2018042709 | 3/2018 |
| JP | 2018187310 | 11/2018 |
| WO | 2004062495 | 7/2004 |

OTHER PUBLICATIONS

"International Search Report (Form PCT/ISA/210) of PCT/JP2020/039629," mailed on Dec. 8, 2020, with English translation thereof, pp. 1-7.

"Written Opinion of the International Searching Authority (Form PCT/ISA/237)" of PCT/JP2020/039629, mailed on Dec. 8, 2020, with English translation thereof, pp. 1-8.

"Office Action of Japan Counterpart Application" with English translation thereof, issued on Nov. 22, 2022, p. 1-p. 6.

* cited by examiner

MENISCUS PROJECTION PLANE SETTING APPARATUS, MENISCUS PROJECTION PLANE SETTING METHOD, AND MENISCUS PROJECTION PLANE SETTING PROGRAM

CROSS-REFERENCE TO RELATED APPLICATIONS

This application is a Continuation of PCT International Application No. PCT/JP2020/039629 filed on Oct. 21, 2020, which claims priority under 35 U.S.C § 119(a) to Japanese Patent Application No. 2019-223582 filed on Dec. 11, 2019. Each of the above application(s) is hereby expressly incorporated by reference, in its entirety, into the present application.

BACKGROUND OF THE INVENTION

1. Field of the Invention

The present disclosure relates to a meniscus projection plane setting apparatus, a meniscus projection plane setting method, and a non-transitory computer readable recording medium storing a meniscus projection plane setting program that set a projection plane when generating a projection image of a meniscus from a three-dimensional image including a knee joint.

2. Description of the Related Art

In recent years, by the progression of medical equipment such as a computed tomography (CT) apparatus and a magnetic resonance imaging (MM) apparatus, a high-quality, high-resolution three-dimensional image has been used for image diagnosis. Since a three-dimensional image is constituted by a large number of two-dimensional images and has a large amount of information, it may take time for a physician to find a desired observation body part for diagnosis. Thus, the diagnosis efficiency may be increased by increasing the visibility of the whole organ or a lesion in the following manner. An organ of interest is recognized and extracted from a three-dimensional image including the organ of interest by using a method such as a maximum intensity projection (MIP) method or a minimum intensity projection (Min IP) method to display an MIP image, or to display a three-dimensional image by volume rendering (VR).

On the other hand, osteoarthritis is a disease that commonly occurs in elder people. In particular, knee osteoarthritis causes pain in the knee joint and reduction in a movement range, and thus, the progression of the symptoms may disable the patient from walking. For diagnosis of such osteoarthritis, knee joint cartilages need to be evaluated qualitatively. Thus, various methods for quantifying knee joint cartilages using a three-dimensional image have been proposed. For example, JP2018-042709A proposes a method in which a projection direction of a cartilage region extracted from an Mill image is determined, the cartilage region is projected in the determined projection direction to generate a projection image, and a quantitative value of the cartilage region is derived in the projection image. By using the method described in JP2018-042709A, a region for quantifying the cartilage region can be determined appropriately, and thus, a stable diagnosis result for the cartilages can be obtained. In particular, by using a quantitative value as the thickness of the cartilages, the thickness of the cartilages can be evaluated.

In addition, JP2013-533765A proposes a method in which the head center, radius, and neck axis of an articular bone are determined from a three-dimensional image of a joint in order to identify a spherical joint such as a femoral neck. In the method described in JP2013-533765A, a three-dimensional neck minimal curve is determined on a three-dimensional surface model of a neck portion of a bone; a least squares fitting plane to the three-dimensional neck minimal curve is determined; the orthogonal direction to the least squares fitting plane is computed as the direction of a precise neck axis; the center of the projection of the three-dimensional neck minimal curve on the least squares fitting plane is computed as a point of the precise neck axis.

SUMMARY OF THE INVENTION

Although causes of the knee osteoarthritis have not been clarified yet, one of the causes of the knee osteoarthritis is thought to be deformation and tearing of menisci, which are present at a knee joint. For example, it is thought that the knee osteoarthritis progresses because cartilages are lost due to deformation, tearing, or deviation of the menisci. Thus, it is important to evaluate the state of menisci quantitatively for diagnosis of knee osteoarthritis. To evaluate the menisci quantitatively, a projection plane for projecting the menisci in a three-dimensional image of a knee joint needs to be set appropriately.

However, the knee joint includes a curved surface. In particular, although a tibial joint appears to be flat, inclinations are different in the medial condyle and the lateral condyle, and the joint surface has a depressed shape. Thus, even if the method described in JP2018-042709A is used, an error in quantifying the menisci becomes large unless the projection direction is set appropriately. For example, as illustrated in FIG. 25, it is assumed that, out of a meniscus 91A and a meniscus 91B on a joint surface of a tibia 90, the meniscus 91B on the joint surface on the lateral condyle side of the tibia 90 is projected in the direction of an arrow A that inclines with respect to a central axis C0 of the tibia 90. In this case, as illustrated in FIG. 26, if there is a lost portion 92 due to damage or the like of the meniscus 91B as indicated by the oblique lines, the lost portion 92 is projected as if the meniscus 91B is present on a projection image 93. In addition, the method described in JP2013-533765A determines the axis in a spherical joint and is not to appropriately set a projection plane for projecting the knee joint.

The present disclosure has been made in view of the above circumstances, and an object thereof is to appropriately set a projection plane for generating a projection image of a meniscus from a three-dimensional image including a joint.

A meniscus projection plane setting apparatus according to the present disclosure includes at least one processor configured to: acquire a three-dimensional image of a knee joint; and set a plane that approximates a joint surface of the knee joint as a projection plane for generating a projection image by projecting a meniscus at the knee joint included in the three-dimensional image.

In the meniscus projection plane setting apparatus according to the present disclosure, the processor may be configured to exclude, from among pixel positions on the joint surface, a pixel position whose distance from the projection plane is greater than or equal to a predetermined threshold and set a new projection plane.

In the meniscus projection plane setting apparatus according to the present disclosure, the processor may be configured to set the projection plane by repeating excluding of the pixel position and setting of the new projection plane a plurality of times.

In the meniscus projection plane setting apparatus according to the present disclosure, the processor may be configured to set the plane that approximates the joint surface by a least squares method.

In the meniscus projection plane setting apparatus according to the present disclosure, the knee joint may be a tibial joint.

In the meniscus projection plane setting apparatus according to the present disclosure, the processor may be configured to extract, as a joint surface region, a region excluding a region between condyles from an image in which a joint surface of the tibia is viewed in a predetermined direction and set, as the projection plane, a plane that approximates the joint surface included in the joint surface region.

In the meniscus projection plane setting apparatus according to the present disclosure, the processor may be configured to generate the projection image by further projecting the meniscus at the knee joint in the three-dimensional image in a direction orthogonal to the projection plane.

In the meniscus projection plane setting apparatus according to the present disclosure, the processor may be configured to generate the projection image by further projecting the meniscus at the knee joint in the three-dimensional image in a direction orthogonal to the projection plane such that a line connecting a center of gravity of a joint surface of a medial condyle of the tibia and a center of gravity of a joint surface of a lateral condyle of the tibia is oriented in a predetermined direction.

In the meniscus projection plane setting apparatus according to the present disclosure, the processor may be configured to generate the projection image by further projecting the meniscus at the knee joint in the three-dimensional image in a direction orthogonal to the projection plane such that an Akagi line at the tibia when viewed in a direction perpendicular to the projection plane is oriented in a predetermined direction.

The "Akagi line" is a line connecting a posterior cruciate ligament attachment and the medial border of a patellar tendon attachment.

In the meniscus projection plane setting apparatus according to the present disclosure, the processor may be configured to further cause a display to display the projection image.

In the meniscus projection plane setting apparatus according to the present disclosure, the processor may be configured to further derive a quantitative value of the meniscus in the projection image.

In the meniscus projection plane setting apparatus according to the present disclosure, the processor may be configured to derive, as the quantitative value, at least one of an area of the meniscus, a volume of the meniscus, a lost area of the meniscus, a representative value of a thickness of the meniscus, or thicknesses of the meniscus at positions of the projection image.

In the meniscus projection plane setting apparatus according to the present disclosure, the processor may be configured to generate a thickness map of the meniscus in a case of deriving the thicknesses of the meniscus at the positions of the projection image.

In the meniscus projection plane setting apparatus according to the present disclosure, the processor may be configured to further cause a display to display the thickness map.

In the meniscus projection plane setting apparatus according to the present disclosure, the processor may be configured to derive the quantitative value of the meniscus within or out of a region of interest at the knee joint in the three-dimensional image in the projection image.

In the meniscus projection plane setting apparatus according to the present disclosure, the region of interest may be a region where a subchondral bone region or a cartilage is supposed to be present at the knee joint.

In the meniscus projection plane setting apparatus according to the present disclosure, the processor is configured to set, in a case where there is a derived result of another quantitative value derived from another three-dimensional image whose imaging timing is different for a same test subject as a test subject for which the three-dimensional image is acquired, the region of interest at a same position as a position of the region of interest in deriving the other quantitative value.

In the meniscus projection plane setting apparatus according to the present disclosure, the processor may be configured to derive, as the quantitative value, a coverage of the meniscus in the region of interest.

In the meniscus projection plane setting apparatus according to the present disclosure, the processor may be configured to derive, as the quantitative value, at least one of a volume of the meniscus out of the region of interest, an area of the meniscus out of the region of interest, or a thickness of the meniscus out of the region of interest.

In the meniscus projection plane setting apparatus according to the present disclosure, the processor may be configured to divide the meniscus in the projection image into a plurality of regions and derive the quantitative value in each of the regions obtained by dividing.

In the meniscus projection plane setting apparatus according to the present disclosure, the processor may be configured to set, in a case where there is another projection image generated from another three-dimensional image whose imaging timing is different for a same test subject as a test subject for which the three-dimensional image is acquired, a projection plane, by which the other projection image is generated, as the projection plane for generating the projection image by projecting the three-dimensional image.

A meniscus projection plane setting method according to the present disclosure includes: acquiring a three-dimensional image of a knee joint; and setting a plane that approximates a joint surface of the knee joint as a projection plane for generating a projection image by projecting a meniscus at the knee joint included in the three-dimensional image.

It is also possible to provide a non-transitory computer readable recording medium storing a program for causing a computer to execute the meniscus projection plane setting method according to the present disclosure.

According to the present disclosure, it is possible to appropriately set a projection plane for generating a projection image of a meniscus from a three-dimensional image including a joint.

DESCRIPTION OF THE PREFERRED EMBODIMENTS

Figure 1:
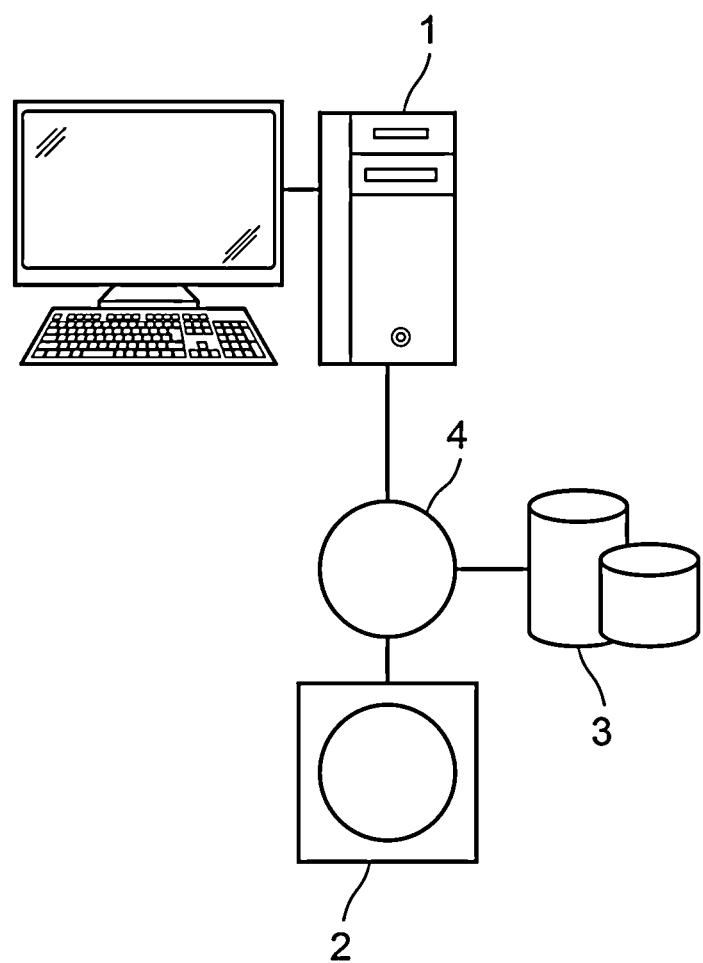
FIG. 1 is a hardware configuration diagram illustrating an overall diagnosis support system to which a meniscus projection plane setting apparatus according to an embodiment of the present disclosure is applied.

Now, an embodiment of the present disclosure will be described with reference to the drawings. FIG. 1 is a hardware configuration diagram illustrating an overall diagnosis support system to which a meniscus projection plane setting apparatus according to the embodiment of the present disclosure is applied. As illustrated in FIG. 1, in the diagnosis support system, a meniscus projection plane setting apparatus 1 according to the present embodiment, a three-dimensional imaging apparatus 2, and an image storage server 3 are communicably connected via a network 4.

The three-dimensional imaging apparatus 2 is an apparatus that images a diagnosis-target body part of a test subject thereby generating a three-dimensional image representing the body part. Specifically, the three-dimensional imaging apparatus 2 is a CT apparatus, an MRI apparatus, a positron emission tomography (PET) apparatus, or the like. A three-dimensional image generated by the three-dimensional imaging apparatus 2 is transmitted to the image storage server 3 and is stored therein. Note that in the present embodiment, the diagnosis-target body part of a patient who is a test subject is a knee joint, the three-dimensional imaging apparatus 2 is an MRI apparatus, and an MM image of the test subject's knee joint is generated by the three-dimensional imaging apparatus 2 as a three-dimensional image.

The image storage server 3 is a computer that stores and manages various types of data and includes an external mass storage device and database management software. The image storage server 3 communicates with the other apparatuses via the network 4 by wire or wirelessly to transmit and receive image data or the like. Specifically, the image storage server 3 acquires various types of data including image data of a three-dimensional image or the like generated by the three-dimensional imaging apparatus 2 via the network and stores the image data in a recording medium such as the external mass storage device to manage the image data. Note that the form of storage of image data and communication between the apparatuses via the network 4 conform to a protocol such as Digital Imaging and Communication in Medicine (DICOM).

The meniscus projection plane setting apparatus 1 is a single computer in which a meniscus projection plane setting program according to the present disclosure is installed. The computer may be a workstation or a personal computer that a physician who performs diagnosis directly operates, or may be a server computer connected to the work station or personal computer via the network. The meniscus projection plane setting program is stored in a storage device of the server computer connected to the network or a network storage in an externally accessible state, is downloaded to a computer used by a physician on demand, and is installed. Alternatively, the meniscus projection plane setting program is recorded on a recording medium such as a digital versatile disc (DVD) or a compact disc read only memory (CD-ROM), is distributed, and is installed in a computer from the recording medium.

Figure 2:
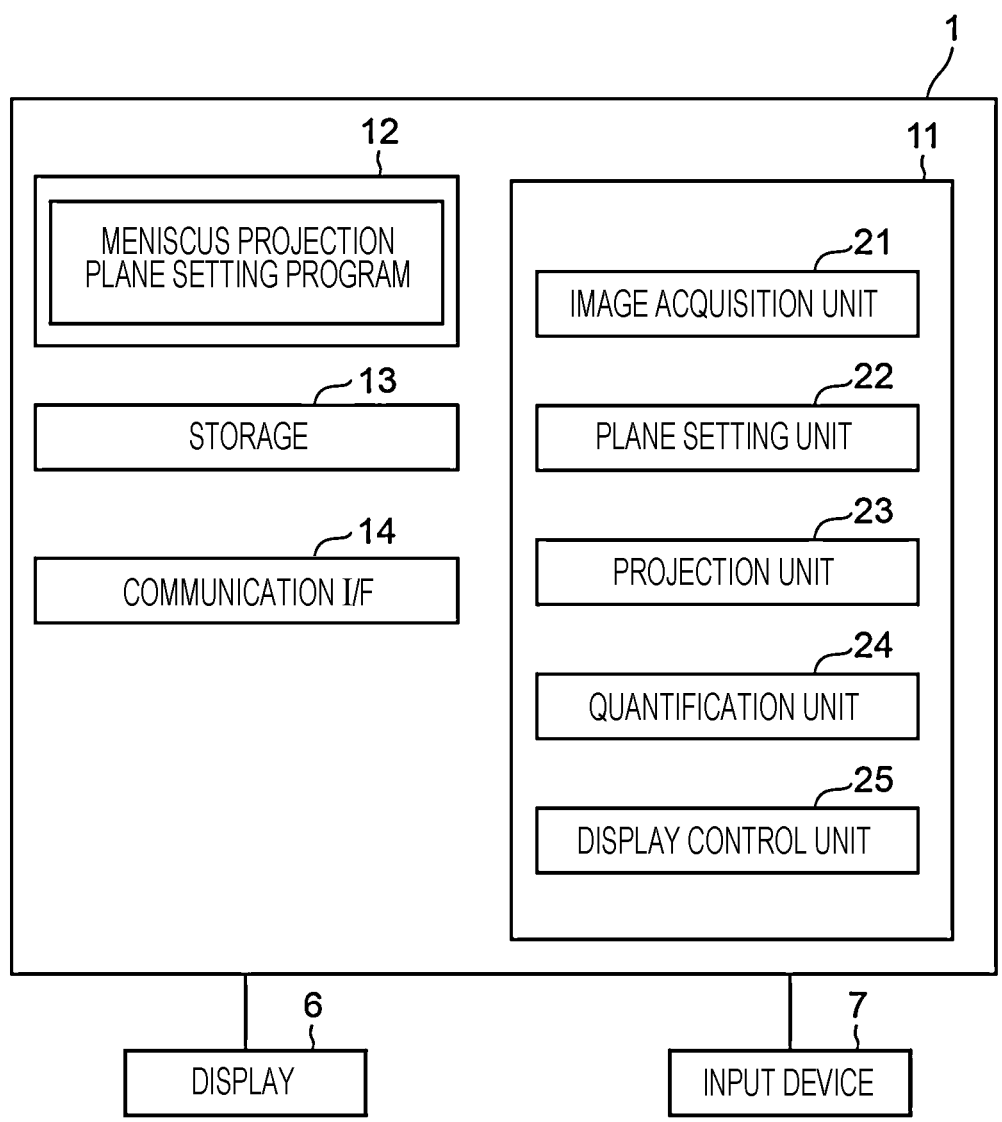
FIG. 2 is a schematic block diagram illustrating a configuration of the meniscus projection plane setting apparatus according to the embodiment.

FIG. 2 is a diagram illustrating a schematic configuration of the meniscus projection plane setting apparatus according to the embodiment of the present disclosure, implemented by the meniscus projection plane setting program being installed in a computer. As illustrated in FIG. 2, the meniscus projection plane setting apparatus 1 includes a central processing unit (CPU) 11, a memory 12, a storage 13, and a communication interface (I/F) 14 as a configuration of a standard workstation. In addition, a display 6 and an input device 7 such as a mouse or a keyboard is connected to the meniscus projection plane setting apparatus 1.

Various types of information are stored in the storage 13. The various types of information include a three-dimensional image of a test subject and information necessary for processing, which are acquired from the image storage server 3 via the network 4. Note that this embodiment assumes that a three-dimensional image V0 in which a knee joint of a test subject is a diagnosis-target body part is stored in the storage 13.

The communication I/F 14 is a network interface for controlling transmission of various types of information to/from an external apparatus such as the image storage server 3 via the network 4.

In the memory 12, the meniscus projection plane setting program read out by the CPU 11 is temporarily stored. As processing to be executed by the CPU 11, the meniscus projection plane setting program prescribes an image acquisition process in which the three-dimensional image V0 of the knee joint is acquired; a plane setting process in which a plane that approximates a joint surface of the knee joint is set as a projection plane for generating a projection image, which will be described later, by projecting menisci at the knee joint included in the three-dimensional image; a projection process in which the menisci are projected onto the projection plane and the projection image is generated; a quantification process in which a quantitative value of the menisci is derived on the projection image; and a display control process in which the quantitative value derived by the quantification is displayed on the display 6.

By the CPU 11 executing these processes in accordance with the program, the computer functions as an image acquisition unit 21, a plane setting unit 22, a projection unit 23, a quantification unit 24, and a display control unit 25.

Figure 3:
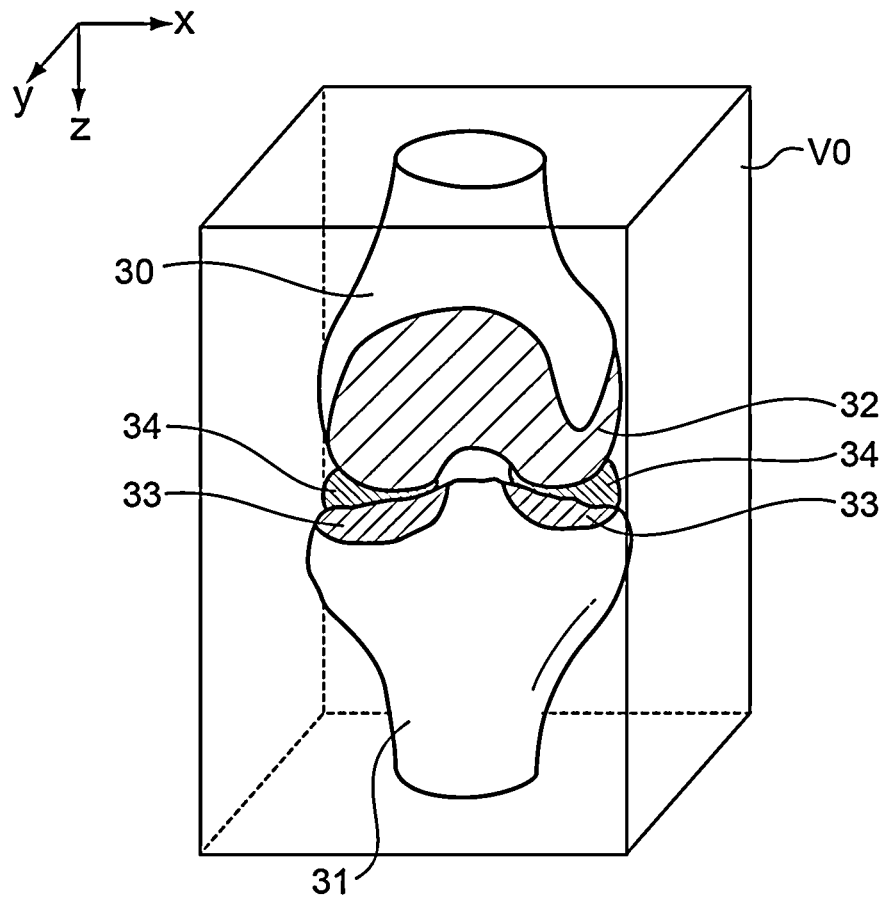
FIG. 3 is a diagram illustrating a three-dimensional image of a knee joint.

The image acquisition unit 21 acquires the three-dimensional image V0 of the knee joint of the test subject from the image storage server 3. Note that, in a case where the three-dimensional image V0 is already stored in the storage 13, the image acquisition unit 21 may acquire the three-dimensional image V0 from the storage 13. FIG. 3 is a diagram illustrating the three-dimensional image V0 of the knee joint. As illustrated in FIG. 3, the three-dimensional image V0 includes a femur 30 and a tibia 31. Note that a patella is omitted from FIG. 3 for description. There are a cartilage 32 in a portion of the femur 30 facing the tibia 31 and a cartilage 33 in a portion of the tibia 31 facing the femur 30. In addition, there are menisci 34 between the cartilage 32 and the cartilage 33. In the present embodiment, the three-dimensional image V0 is an MRI image, and the range of signal values (voxel values) in the three-dimensional image V0 differs in each of a bone region, a cartilage region, a meniscus region, and other muscle, fat, etc. regions. The image acquisition unit 21 extracts a bone region and a meniscus region from the three-dimensional image V0 through a threshold process on the signal values. Specifically, a region of a range corresponding to a signal value of a bone is extracted as the bone region from the three-dimensional image V0. In addition, a region of a range corresponding to a signal value of a meniscus is extracted as the meniscus region from the three-dimensional image V0. Note that the image acquisition unit 21 may also extract a cartilage region from the three-dimensional image V0. In this case, the image acquisition unit 21 extracts a region of a range corresponding to a signal value of a cartilage as the cartilage region from the three-dimensional image V0. The bone region includes the femur 30 and the tibia 31, the cartilage region includes the cartilages 32 and 33, and the meniscus region includes the menisci 34.

The image acquisition unit 21 extracts the bone region, the cartilage region, and the meniscus region from the three-dimensional image V0 in the present embodiment, but the present disclosure is not limited to this. A means that extracts the bone region, the cartilage region, and the meniscus region from the three-dimensional image V0 may be additionally provided. Note that in the present embodiment, the cartilage 33 of the tibia 31 is extracted as the cartilage region. In addition, extraction of the bone region, the cartilage region, and the meniscus region from the three-dimensional image V0 is not limited to the threshold process. For example, a determiner that has been subjected to machine learning by deep learning or the like so as to extract the bone region, the cartilage region, and the meniscus region from the three-dimensional image V0 may be used.

On the other hand, when the three-dimensional imaging apparatus 2 acquires the three-dimensional image V0, the knee joint is imaged in a state where the knee is stretched or slightly bended (10 to 20 degrees). In the three-dimensional image V0, as illustrated in FIG. 3, the direction in which the femur 30 and the tibia 31 extend from top to bottom is set as z direction, the direction from back to front when viewing the knee joint from the front is set as y direction, and the direction from left to right when viewing the knee joint from the front is set as x direction.

Figure 4:
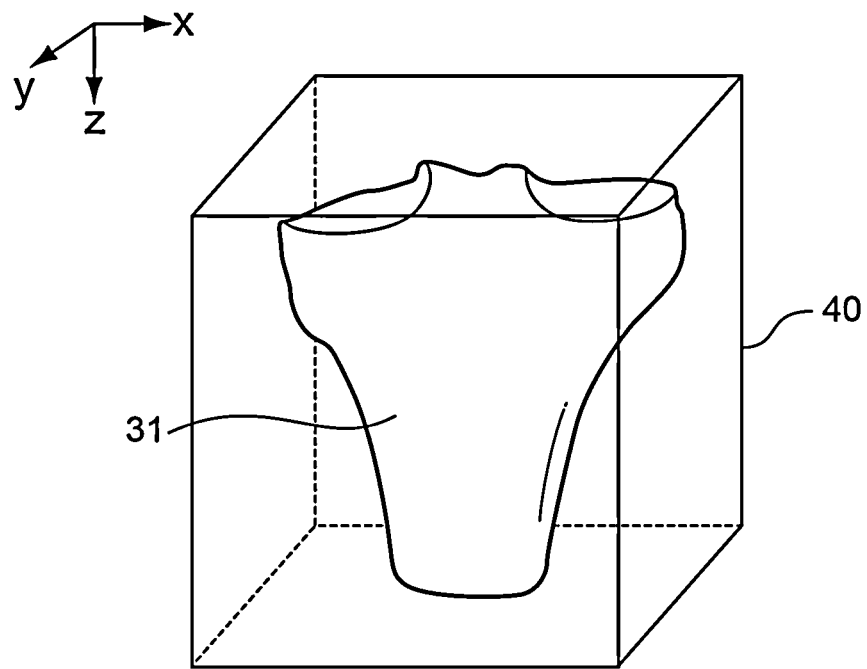
FIG. 4 is a diagram illustrating a three-dimensional region.

The plane setting unit 22 sets a plane that approximates a joint surface of the knee joint as a projection plane for generating a projection image, which will be described later, by projecting the three-dimensional image V0, more specifically, menisci at the knee joint included in the three-dimensional image V0. Now, a process performed by the plane setting unit 22 will be described. First, the plane setting unit 22 sets a minimal three-dimensional region surrounding the tibia 31 included in the three-dimensional image V0. FIG. 4 is a diagram illustrating the three-dimensional region. As illustrated in FIG. 4, the plane setting unit 22 sets a minimal three-dimensional region 40 surrounding the tibia 31. Note that directions of the sides of the three-dimensional region 40 are made to match the x direction, the y direction, and the z direction of the three-dimensional image V0.

Figure 5:
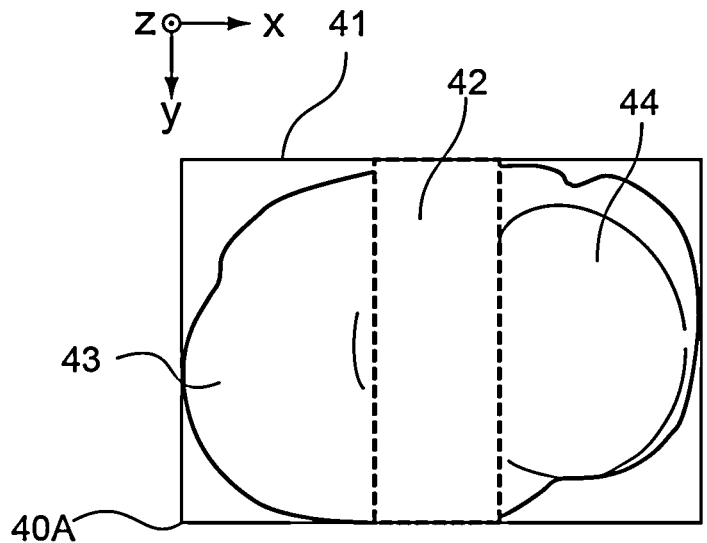
FIG. 5 is a diagram for describing extraction of joint surface regions.

Subsequently, the plane setting unit 22 extracts, as a joint surface region, a region excluding a region between condyles from a top surface 40A of the three-dimensional region 40. FIG. 5 is a diagram for describing extraction of joint surface regions. As illustrated in FIG. 5, the plane setting unit 22 sets, as a region 42 between condyles, a region having a width that corresponds to a predetermined ratio to the length of a side 41 on the basis of the middle point of the side 41 extending in the x direction of the top surface 40A. Note that the predetermined ratio may be 15 to 25%, preferably 20%, but the present disclosure is not limited to this. Then, the plane setting unit 22 sets, as joint surface regions 43 and 44, two regions that are on the left and right of the region 42 between condyles on the top surface 40A. Note that the joint surface region 43 corresponds to a region on the medial condyle side in the joint of the tibia 31 and the joint surface region 44 corresponds to a region on the lateral condyle side in the joint of the tibia 31.

Figure 6:
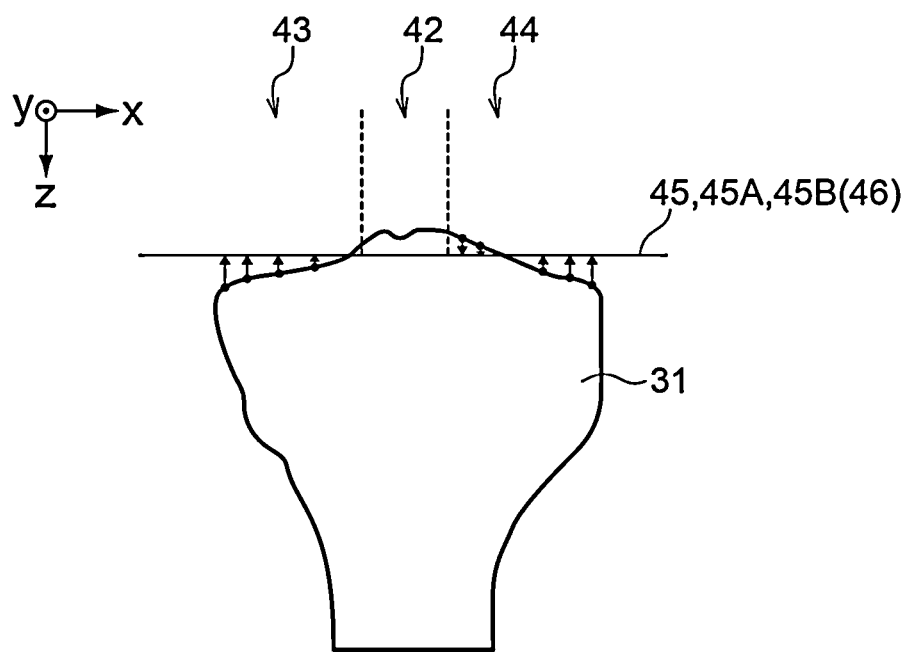
FIG. 6 is a diagram for describing deriving of a projection plane.

Subsequently, the plane setting unit 22 sets, as the projection plane, a plane that approximates a joint surface included in the joint surface regions 43 and 44. Specifically, the plane setting unit 22 derives, as the projection plane, a plane on which distances from voxels constituting the joint surface included in the joint surface regions 43 and 44 are minimal by the least squares method. FIG. 6 is a diagram for describing deriving of the projection plane. Note that a cross section perpendicular to the y axis of the tibia 31 is illustrated in FIG. 6 for easy description. In addition, only some of the voxels in the joint surface regions 43 and 44 are represented by the black circles, while the distances from the voxels to the plane, that is, a projection plane 45, are represented by the arrows. As illustrated in FIG. 6, the plane setting unit 22 derives, as the projection plane 45, a plane on which the sum total of the distances from the voxels in the joint surface regions 43 and 44 is minimal.

Figure 7:
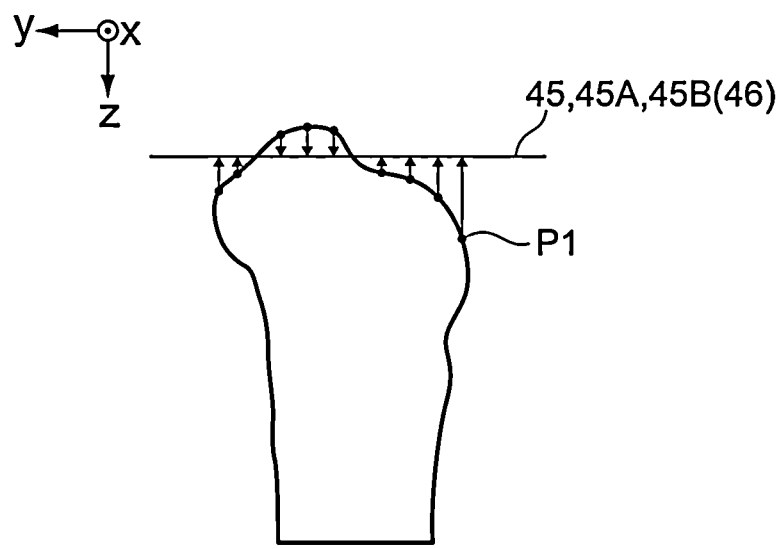
FIG. 7 is a diagram for describing exclusion of a voxel.

Subsequently, the plane setting unit 22 sets a new projection plane by excluding a voxel whose distance corresponds to a predetermined ratio from the maximum among the distances from the voxels in the joint surface regions 43 and 44 to the projection plane 45. FIG. 7 is a diagram for describing exclusion of the voxel. Note that FIG. 7 illustrates a cross section of the tibia 31 in the zy plane. In the present embodiment, the plane setting unit 22 derives the projection plane 45 on which the distances from the voxels constituting the joint surface included in the joint surface regions 43 and 44 are minimal. However, on the joint surface, there is a voxel whose distance from the projection plane 45 is larger than the other voxels, as in a voxel P1 illustrated in FIG. 7. If the projection plane is set by using such a voxel, it is not possible to derive the plane that approximates a joint surface accurately.

Accordingly, the plane setting unit 22 excludes the voxel whose distance corresponds to the predetermined ratio from the maximum among the distances from the voxels in the joint surface regions 43 and 44 to the projection plane 45. Then, by using voxels other than the excluded voxel, the plane setting unit 22 derives, as a new projection plane 45A, a plane for which the sum total of the distances from the voxels in the joint surface regions 43 and 44 is minimal. Here, the predetermined ratio may be 5 to 20%, preferably 10%, but the present disclosure is not limited to this.

In the present embodiment, the plane setting unit 22 repeatedly performs the above process such that a voxel whose distance corresponds to the predetermined ratio from the maximum among the distances from the voxels in the joint surface regions 43 and 44 to the new projection plane 45A is further excluded and a new projection plane 45B is set, to derive a final projection plane 46. For example, when the process of setting a new projection plane is repeated twice, in a case where the above predetermined ratio is 10%, the ratio of voxels that contribute to the setting of the projection plane 46 is 81% of all the voxels in the joint surface regions 43 and 44. Note that the present embodiment assumes that the above predetermined ratio is 10% and that the process of setting a new projection plane is repeated twice.

Figure 8:
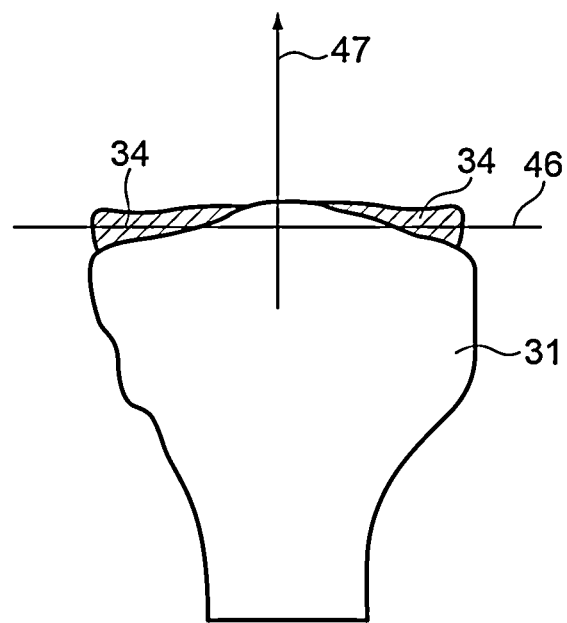
FIG. 8 is a diagram for describing generation of a projection image.

The projection unit 23 generates a projection image by projecting the menisci at the joint in the three-dimensional image V0 in the direction orthogonal to the projection plane 46. That is, as illustrated in FIG. 8, the projection unit 23 generates a projection image by projecting the menisci 34 in a direction 47 orthogonal to the projection plane 46. Although the tibia 31 is also projected when the projection image is generated in the present embodiment, only the menisci 34 may be projected to generate the projection image. Note that "orthogonal" includes, not only a case of being completely orthogonal, but also a case of being orthogonal with an error of a certain degree, such as about 1 to 2 degrees.

Figure 9:
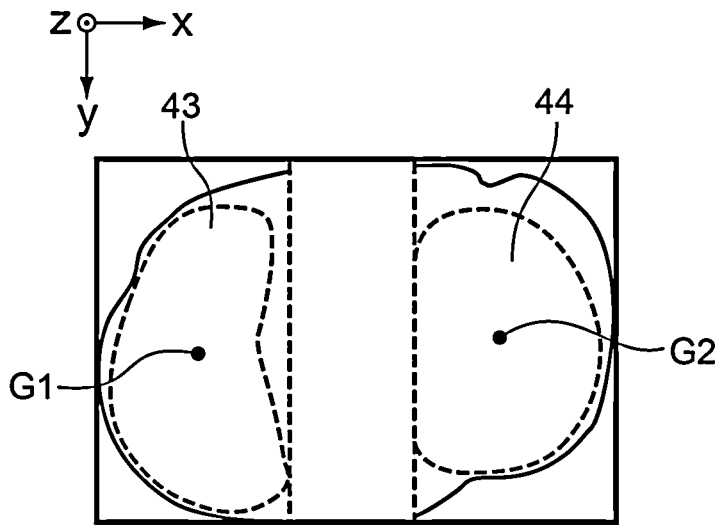
FIG. 9 is a diagram for describing deriving of centers of gravity.

At this time, the projection unit 23 generates the projection image such that a line connecting the center of gravity of a joint surface of the medial condyle of the tibia 31 and the center of gravity of a joint surface of the lateral condyle of the tibia 31 is oriented in a predetermined direction. FIG. 9 is a diagram for describing deriving of the centers of gravity. The voxels to be used when deriving the projection plane 46 is reduced to 81% of all the voxels in the joint surface regions 43 and 44 by repeating the above-described process of setting a new projection plane. In each of the joint surface regions 43 and 44, using only the voxels used for the process of setting the projection plane 46, the projection unit 23 derives the center of gravity of the joint surface of the medial condyle of the tibia 31 and the center of gravity of the joint surface of the lateral condyle of the tibia 31. At this time, a center of gravity G1 of the joint surface of the medial condyle is derived by using the voxels in the joint surface region 43, while a center of gravity G2 of the joint surface of the lateral condyle is derived by using the voxels in the joint surface region 44. Note that FIG. 9 illustrates regions where the voxels used for deriving the center of gravity G1 and the center of gravity G2 are present by surrounding the regions by broken lines.

Figure 10:
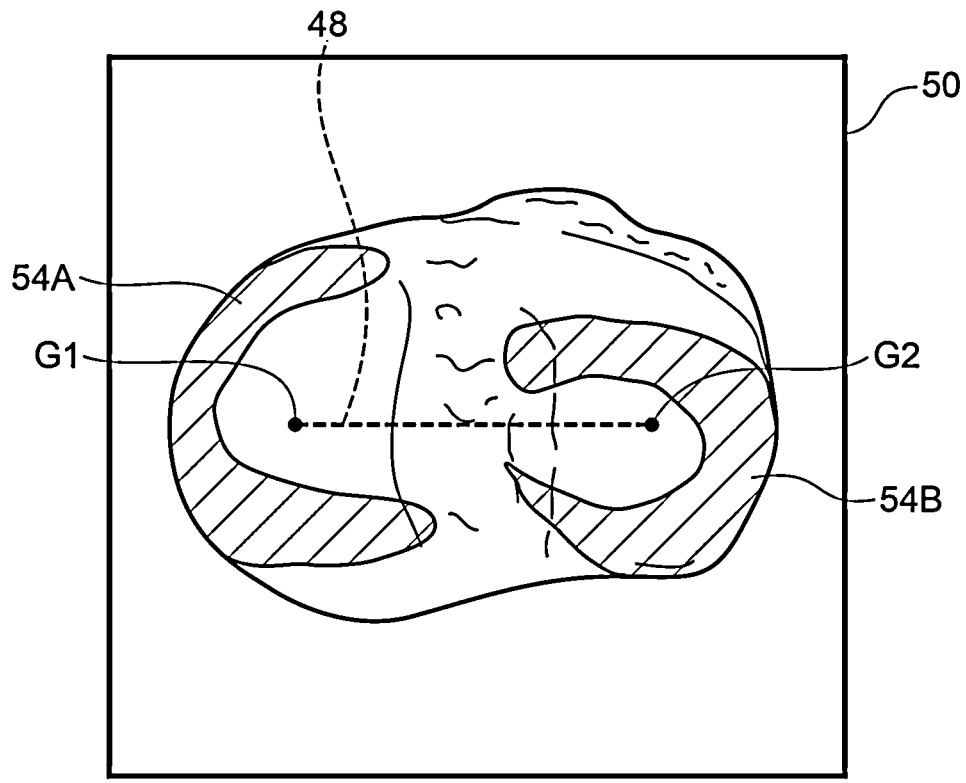
FIG. 10 is a diagram illustrating a projection image including a line connecting the centers of gravity.

The projection unit 23 generates the projection image by projecting the tibia 31 and the menisci 34 in the direction orthogonal to the projection plane 46 such that the line connecting the center of gravity G1 and the center of gravity G2 is horizontal in the projection image. FIG. 10 is a diagram illustrating the projection image of the tibia 31 and the menisci 34. In a projection image 50 illustrated in FIG. 10, a line 48 connecting center of gravity G1 and the center of gravity G2 is horizontal. Note that meniscus regions 54A and 54B are hatched in FIG. 10. The meniscus region 54A corresponds to the medial meniscus, whereas the meniscus region 54B corresponds to the lateral meniscus.

Figure 11:
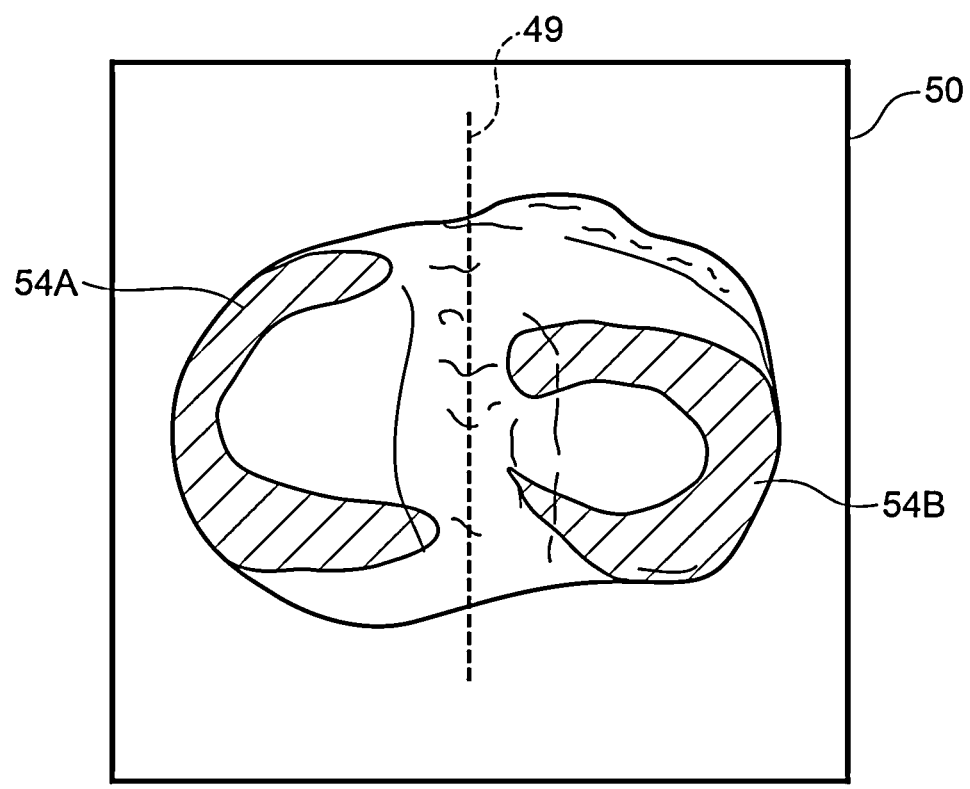
FIG. 11 is a diagram illustrating the projection image including an Akagi line.

Note that an Akagi line may be derived on a joint surface of the tibia 31, and the projection image may be generated by projecting the tibia 31 and the menisci 34 in the direction orthogonal to the projection plane 46 such that the Akagi line is oriented in the perpendicular direction of the projection image. The Akagi line is a line connecting a posterior cruciate ligament attachment and the medial border of a patellar tendon attachment. FIG. 11 is a diagram illustrating the projection image generated such that the Akagi line is oriented in the perpendicular direction of the projection image. Note that as illustrated in FIG. 11, in the projection image 50, an Akagi line 49 is perpendicular.

Figure 12:
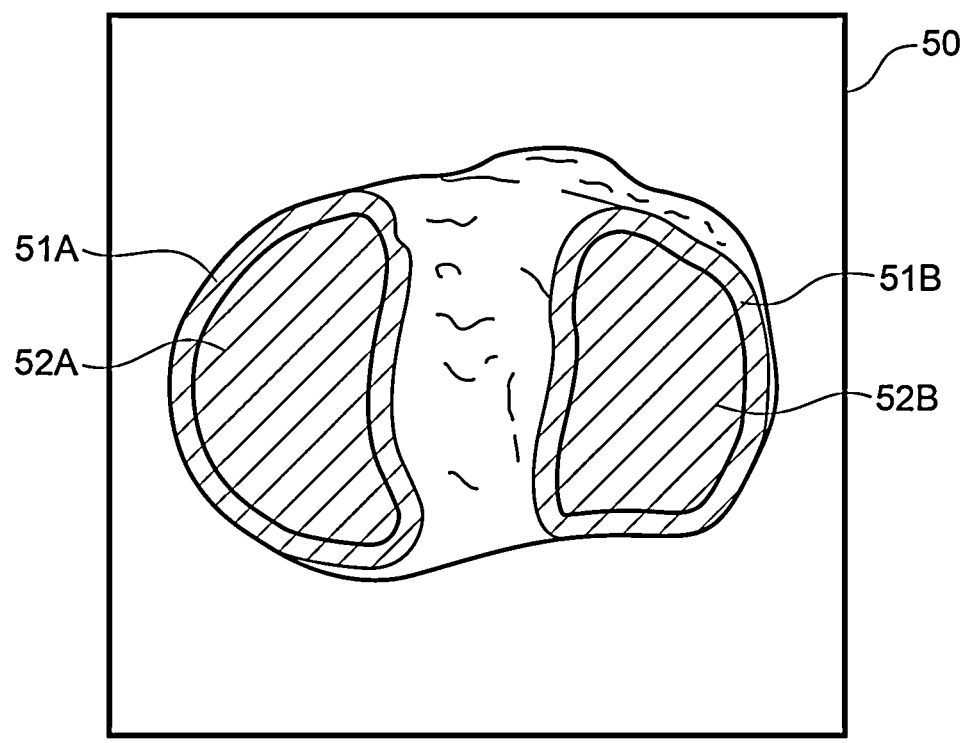
FIG. 12 is a diagram for describing setting of regions of interest.

Furthermore, the projection unit 23 sets a region of interest in the projection image 50. In the present embodiment, the projection unit 23 sets, as regions of interest, regions corresponding to subchondral bone regions at the joint. FIG. 12 is a diagram for describing setting of the regions of interest. In the projection image 50 illustrated in FIG. 12, for describing setting of the subchondral bone regions, the meniscus regions are omitted, and cartilage regions 51A and 51B are illustrated. In addition, in FIG. 12, each of the cartilage region 51A on the joint surface of the medial condyle and the cartilage region 51B on the joint surface of the lateral condyle are hatched.

Here, the subchondral bone regions are regions where the joint of the tibia 31 and the joint of the femur 30 wear each other. The peripheries of the cartilage regions 51A and 51B in the projection image 50 and the joint of the femur 30 do not wear each other. Thus, the projection unit 23 extracts, as the subchondral bone regions, regions excluding regions in predetermined ranges from the edges of the cartilage regions 51A and 51B in the projection image 50, and sets the extracted subchondral bone regions as a region of interest 52A and a region of interest 52B. On the other hand, in the tibia 31, an outline that defines a region in which a cartilage is supposed to be present in the joint is included in the joint surface as a protruding portion. Thus, the projection unit 23 may set the region of interest 52A and the region of interest 52B by regarding, as the cartilage regions 51A and 51B, the regions surrounded by the protruding portions on the joint surface. In addition, the projection unit 23 may include a determiner that has been subjected to machine learning by deep learning or the like so as to extract the subchondral bone regions from the projection image 50, and the subchondral bone regions may be extracted by using the determiner.

The quantification unit 24 derives quantitative values of the meniscus regions 54A and 54B in the projection image

50. A quantitative value is derived for each of the medial meniscus and the lateral meniscus in the present embodiment, but the present disclosure is not limited to this. The quantitative value may be derived by combining the medial meniscus and the lateral meniscus together.

Figure 13:
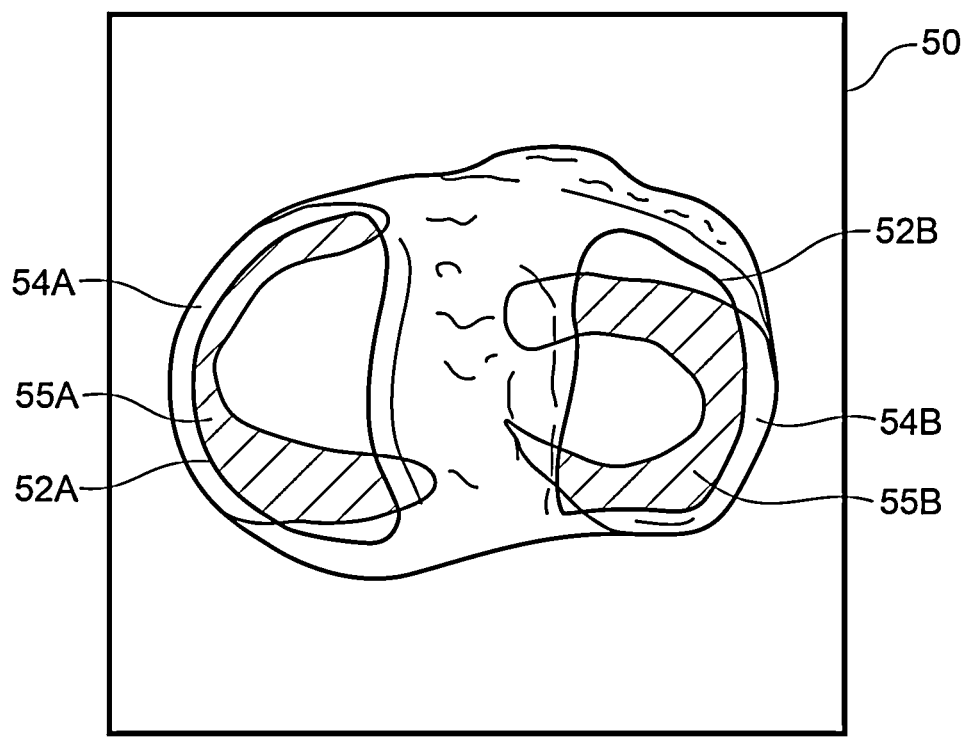
FIG. 13 is a diagram for describing deriving of quantitative values.

FIG. 13 is a diagram for describing deriving of the quantitative values. First, the quantification unit 24 derives the areas of the region of interest 52A and the region of interest 52B and the areas of the meniscus regions 54A and 54B. The quantification unit 24 further derives the areas of meniscus regions 54A and 54B within the region of interest 52A and the region of interest 52B. The areas of meniscus regions 54A and 54B within the region of interest 52A and the region of interest 52B are the areas of in-region-of-interest meniscus regions 55A and 55B hatched in FIG. 13. Here, the area of each pixel is known in the projection image 50. Thus, the quantification unit 24 counts the number of pixels in the region of interest 52A and the region of interest 52B and the meniscus regions 54A and 54B, and multiplies the counted number of pixels by the area per pixel, thereby deriving areas S1A and S1B of the region of interest 52A and the region of interest 52B and areas S2A and S2B of the meniscus regions 54A and 54B. The quantification unit 24 further derives areas S3A and S3B of the meniscus regions 54A and 54B within the region of interest 52A and the region of interest 52B, that is, the in-region-of-interest meniscus regions 55A and 55B. Note that each of the areas S3A and S3B of the in-region-of-interest meniscus regions 55A and 55B is one of the quantitative values. Also, each of the areas S2A and S2B of the meniscus regions 54A and 54B is one of the quantitative values.

In the present embodiment, the quantification unit 24 derives, as one of the quantitative values, each of coverages of the meniscus regions 54A and 54B in the region of interest 52A and the region of interest 52B. The coverage of the meniscus region 54A in the medial region of interest 52A is derived as S3A/S1A, which is the area S3A of the in-region-of-interest meniscus region 55A to the area S1A of the region of interest 52A. The coverage of the meniscus region 54B in the lateral region of interest 52B is derived as S3B/S1B, which is the area S3B of the in-region-of-interest meniscus region 55B to the area S1B of the region of interest 52B.

Figure 14:
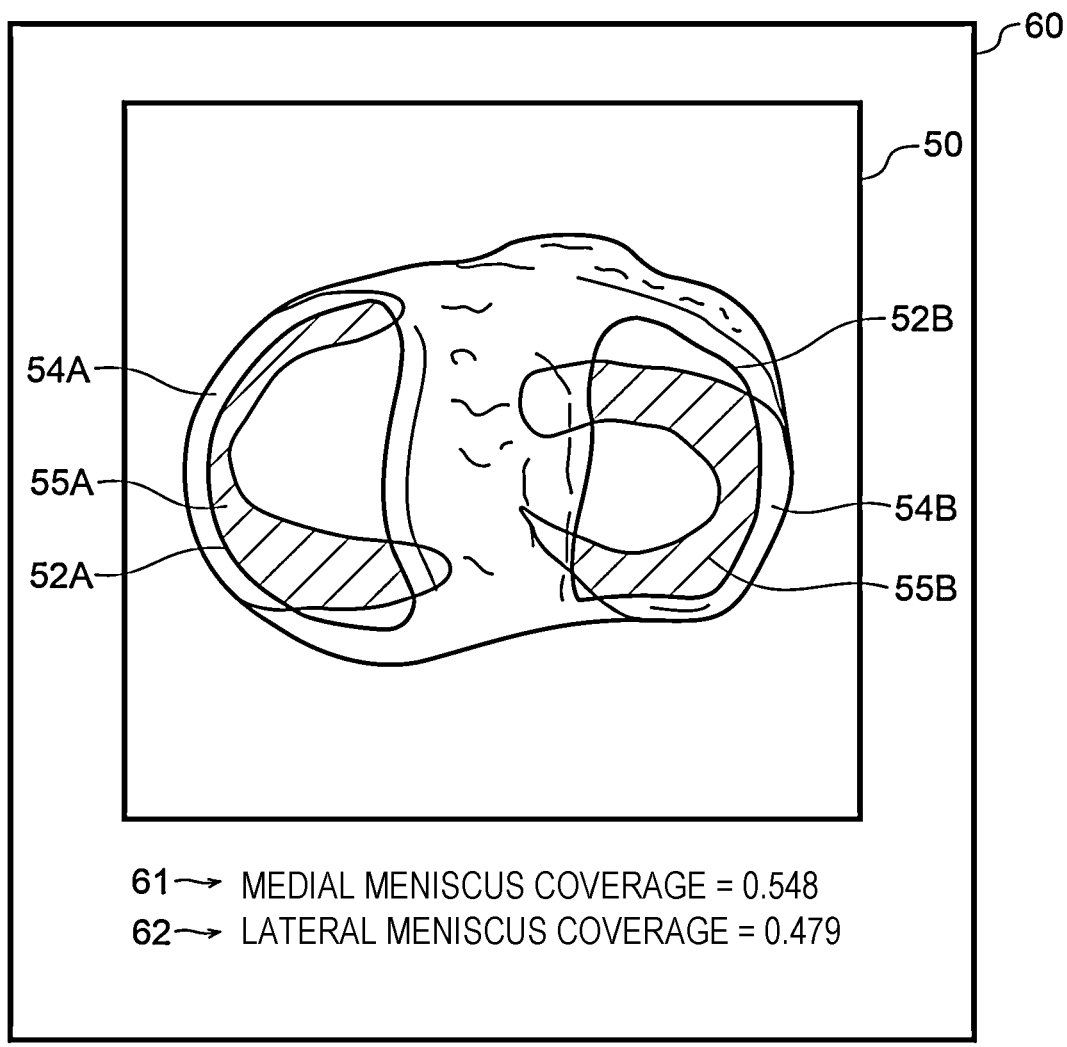
FIG. 14 is a diagram illustrating a display screen of quantitative values of menisci.

FIG. 14 is a diagram illustrating a display screen of the quantitative values of the menisci. As illustrated in FIG. 14, on a display screen 60 of the quantitative values of the menisci, the projection image 50, a coverage 61 of the medial meniscus, and a coverage 62 of the lateral meniscus are displayed. The display screen 60 enables an operator to understand, in addition to the state of the menisci 34, that the coverage 61 of the medial meniscus is 0.548 and the coverage 62 of the lateral meniscus is 0.479.

Note that over-time observation may be performed for the same test subject by comparing a plurality of three-dimensional images whose imaging timings are different. In such a case, in a case where a projection image is generated from a first three-dimensional image V1 whose imaging timing is in the past, a projection image is preferably generated from a second three-dimensional image V2 whose imaging timing is new for over-time observation. Note that the first three-dimensional image V1 corresponds to another three-dimensional image according to the present disclosure. In this case, although the menisci 34 may wear or become deformed over time, the shape of the joint does not become deformed. Thus, upon generating the projection image from the first three-dimensional image V1, information representing the projection plane 46 is preferably stored in the image storage server 3, and the projection image from the second three-dimensional image V2 is preferably generated by acquiring the information of the projection plane stored for the same test subject and using the acquired information of the projection plane.

This can reduce the calculation amount when the projection image from the second three-dimensional image V2 is generated. In addition, in this case, in a case where the region of interest 52A and the region of interest 52B are set in the projection image from the first three-dimensional image V1, the same regions of interest as those in the projection image from the first three-dimensional image V1 are preferably set in the projection image from the second three-dimensional image V2. Thus, the quantitative values of the menisci 34 in the first three-dimensional image V1 and the quantitative values of the menisci 34 in the second three-dimensional image V2 can be temporally compared with each other with ease.

Figure 15:
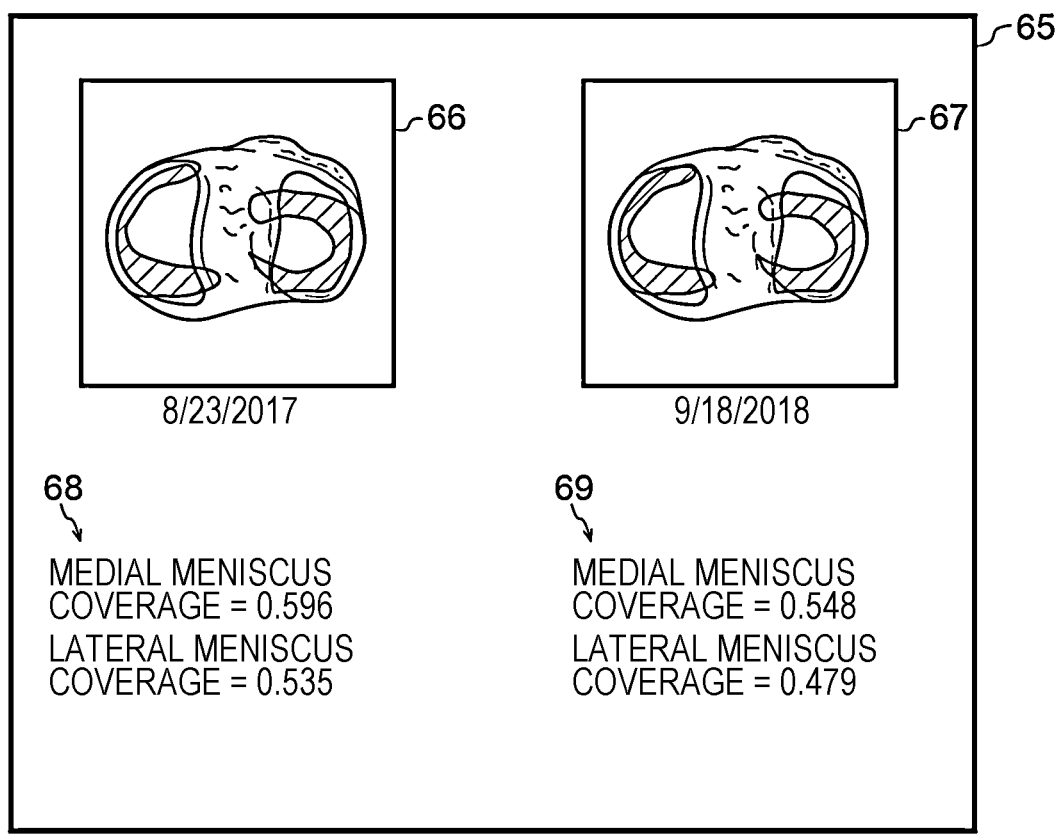
FIG. 15 is a diagram illustrating a display screen for temporal comparison of the quantitative values of the menisci.

FIG. 15 is a diagram illustrating a display screen for temporal comparison of the quantitative values of the menisci. As illustrated in FIG. 15, on a display screen 65 for temporal comparison, a previous projection image 66 acquired during a previous examination and a current projection image 67 acquired during a current examination are displayed. Below the previous projection image 66, an imaging date of the three-dimensional image and coverages (a coverage of the medial meniscus and a coverage of the lateral meniscus) 68 of the meniscus regions in the regions of interest acquired from the previous projection image 66 are displayed. Below the current projection image 67, an imaging date of the three-dimensional image and coverages (a coverage of the medial meniscus and a coverage of the lateral meniscus) 69 of the meniscus regions in the regions of interest acquired from the current projection image 67 are displayed. The display screen 65 enables an operator to understand over-time changes in the menisci 34. In FIG. 15, the imaging date is displayed, however, an imaging time may also be displayed in addition to the imaging date.

Figure 16:
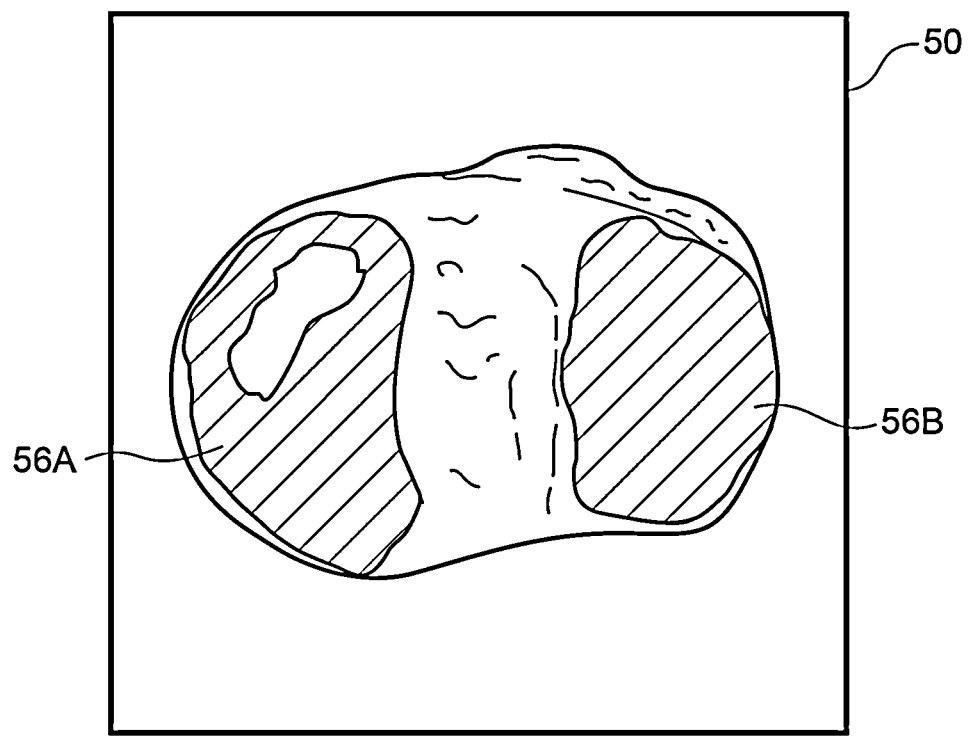
FIG. 16 is a diagram for describing setting of regions of interest.
Figure 17:
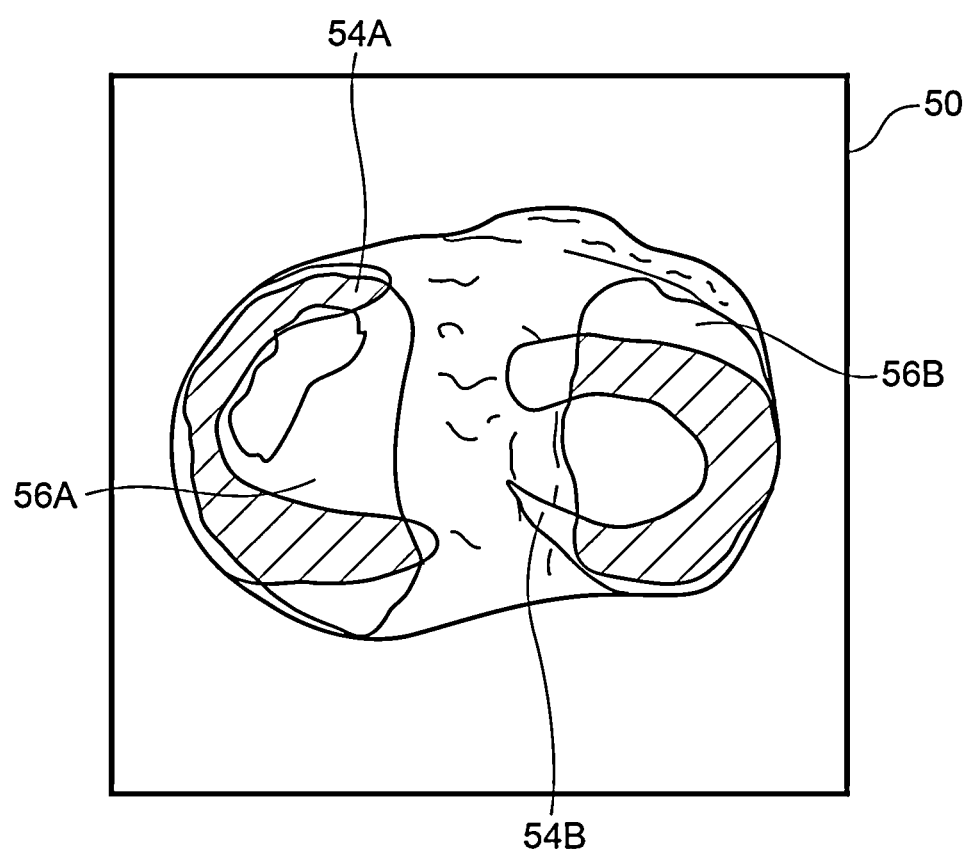
FIG. 17 is a diagram illustrating a projection image of the regions of interest and the menisci.

Note that the region of interest 52A and the region of interest 52B are not limited to the subchondral bone regions. As illustrated in FIG. 16, the cartilage regions may also be set as a region of interest 56A and a region of interest 56B. In this case, the projection image 50 including the meniscus region too is as illustrated in FIG. 17. Note that part of the cartilage is lost on the region of interest 56A side. In a case where coverages of the meniscus regions in the regions of interest are to be derived as the quantitative values in this case, it is assumed that the area of the region of interest 56A is S4A, the area of the region of interest 56B is S4B, the areas of the meniscus regions 54A and 54B within the region of interest 56A and the region of interest 56B are S5A and SSB. Thus, the coverage of the meniscus region 54A in the medial region of interest 56A is derived as S5A/S4A. The coverage of the meniscus region 54B in the lateral region of interest 56B is derived as S5B/S4B.

In addition, although the projection plane is set on the basis of the tibia 31, the projection plane may alternatively be set on the basis of the femur 30. In this case, for example, the projection plane may be set such that the direction in which the central axis of the femur extends is the projection direction.

The quantification unit 24 may also derive the volumes of the menisci 34 as the quantitative values. In this case, the quantification unit 24 may derive the volumes of the menisci 34 by counting the number of pixels of the meniscus regions 54A and 54B in the three-dimensional image and multiplying the number of pixels by the volume per pixel.

Figure 18:
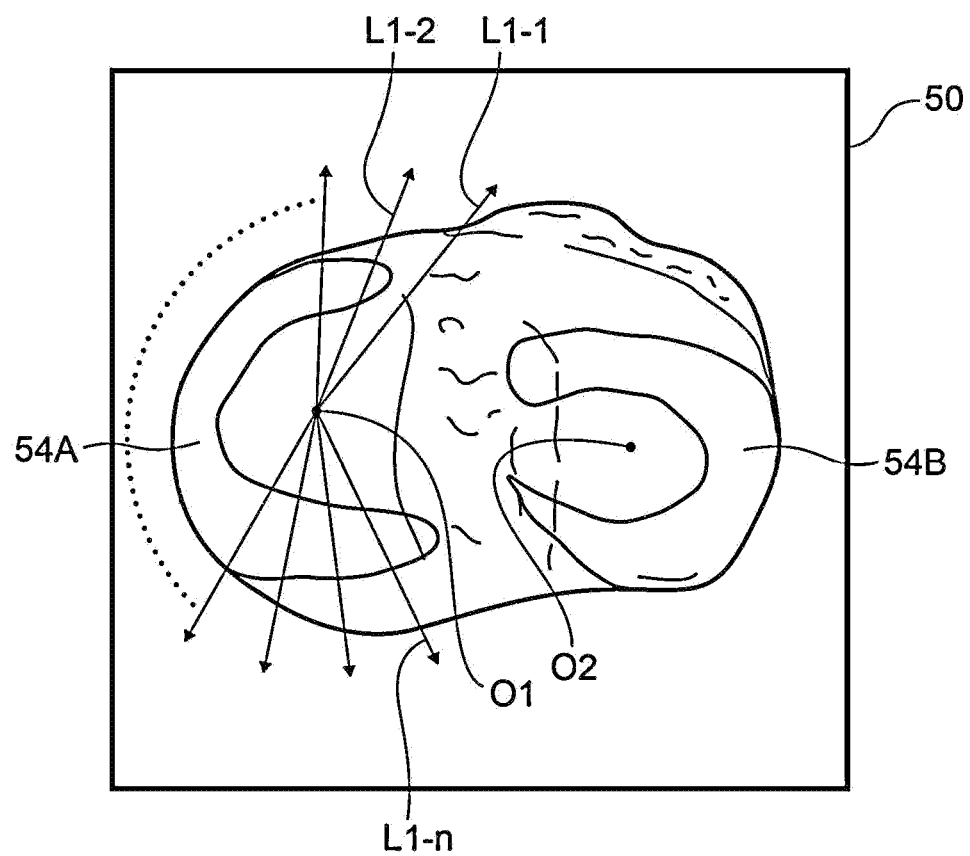
FIG. 18 is a diagram for describing deriving of the thickness of a meniscus.

The quantification unit 24 may also derive the thicknesses of the menisci 34 as the quantitative values. FIG. 18 is a diagram for describing deriving of the thickness of a meniscus. As illustrated in FIG. 18, the quantification unit 24 sets each of reference points O1 and O2 in the projection image 50. The reference point O1 is a point at which the average distance therefrom to the nearest edge of the meniscus region 54A is minimal, but the present disclosure is not limited to this. The reference point O2 is a point at which the average distance therefrom to the nearest edge of the meniscus region 54B is minimal, but the present disclosure is not limited to this. Then, from the reference point O1 as the center, the quantification unit 24 sets a plurality of reference lines L1-1, L1-2 . . . L1-$n$ radially at equiangular intervals as for the medial meniscus region 54A. Then, by using the three-dimensional image V0, the quantification unit 24 derives the average thickness of a meniscus 34 on each reference line. Note that the plurality of reference lines may be set at, for example, 10-degree intervals, but the present disclosure is not limited to this.

Figure 19:
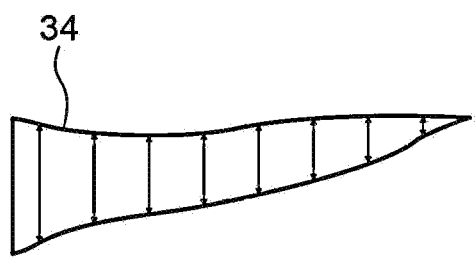
FIG. 19 is diagram for describing deriving of the average thickness of the meniscus.

FIG. 19 is a cross sectional view of the meniscus for describing deriving of the average thickness of the meniscus. Note that FIG. 19 illustrates a cross section of the meniscus 34 on a certain reference line. As illustrated in FIG. 19, the meniscus 34 has a wedge shape in cross section. Thus, as illustrated by the arrows in FIG. 19, the quantification unit 24 derives the thicknesses of the meniscus 34 at a plurality of positions on the reference line, and derives the average of the plurality of thicknesses as the thickness of the meniscus 34 on the reference line. Furthermore, the quantification unit 24 derives the average of the thicknesses of the meniscus 34 on the plurality of reference lines as the thickness of the meniscus 34. Note that only the thickness of the meniscus 34 in the medial meniscus region 54A is derived in FIG. 18 and FIG. 19, but the meniscus 34 in the lateral meniscus region 54B may be derived in the same manner as that for the meniscus 34 in the medial meniscus region 54A.

Note that the thickness of the meniscus 34 on each reference line is one of the quantitative values. Each of the plurality of thicknesses of the meniscus 34 derived on each reference line is also one of the quantitative values. A representative value such as the average, median, minimum, or maximum of the thicknesses of the meniscus 34 related to all the reference lines is also one of the quantitative values.

Figure 20:
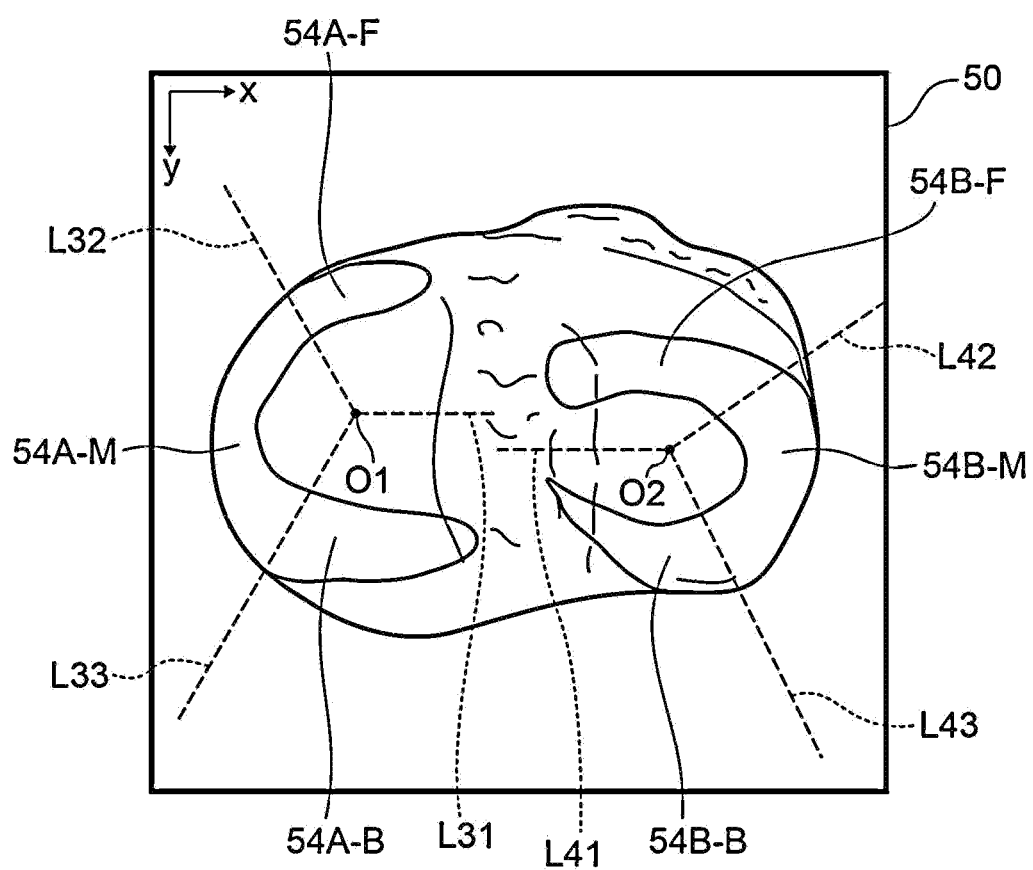
FIG. 20 is a diagram for describing dividing of meniscus regions.

The quantification unit 24 may also divide the meniscus regions 54A and 54B into a plurality of regions and may derive a quantitative value in each of the divided regions. FIG. 20 is a diagram for describing dividing of the meniscus regions. As illustrated in FIG. 20, the quantification unit 24 sets the reference points O1 and O2, which are substantially the same as those in FIG. 18, in the projection image 50. Then, the quantification unit 24 sets a reference line L31 extending in the X direction with the reference point O1 as the origin, and further sets, with the reference point O1 as the origin, reference lines L32 and L33 at which the angles with the reference line L31 are 120 degrees and 240 degrees, respectively, counterclockwise. In addition, the quantification unit 24 sets a reference line L41 extending in the X direction with the reference point O2 as the origin, and further sets, with the reference point O2 as the origin, reference lines L42 and L43 at which the angles with the reference line L41 are 120 degrees and 240 degrees, respectively, clockwise. Then, the quantification unit 24 divides the meniscus region 54A into a front section 54A-F defined by the reference lines L31 and L32, a middle section 54A-M defined by the reference lines L32 and L33, and a back section 54A-B defined by the reference lines L33 and L31. In addition, the quantification unit 24 divides the meniscus region 54B into a front section 54B-F defined by the reference lines L41 and L42, a middle section 54B-M defined by the reference lines L42 and L43, and a back section 54B-B defined by the reference lines L43 and L41.

Then, as for the meniscus region 54A, the quantification unit 24 derives the quantitative value for each of the front section 54A-F, the middle section 54A-M, and the back section 54A-B. In addition, as for the meniscus region 54B, the quantification unit 24 derives the quantitative value for each of the front section 54B-F, the middle section 54B-M, and the back section 54B-B. Note that the area, volume, and thickness in the meniscus regions 54A and 54B can be used as the quantitative value of each divided region. In addition, the coverage in the meniscus regions 54A and 54B within the regions of interest may also be derived as the quantitative value of each divided region.

Figure 21:
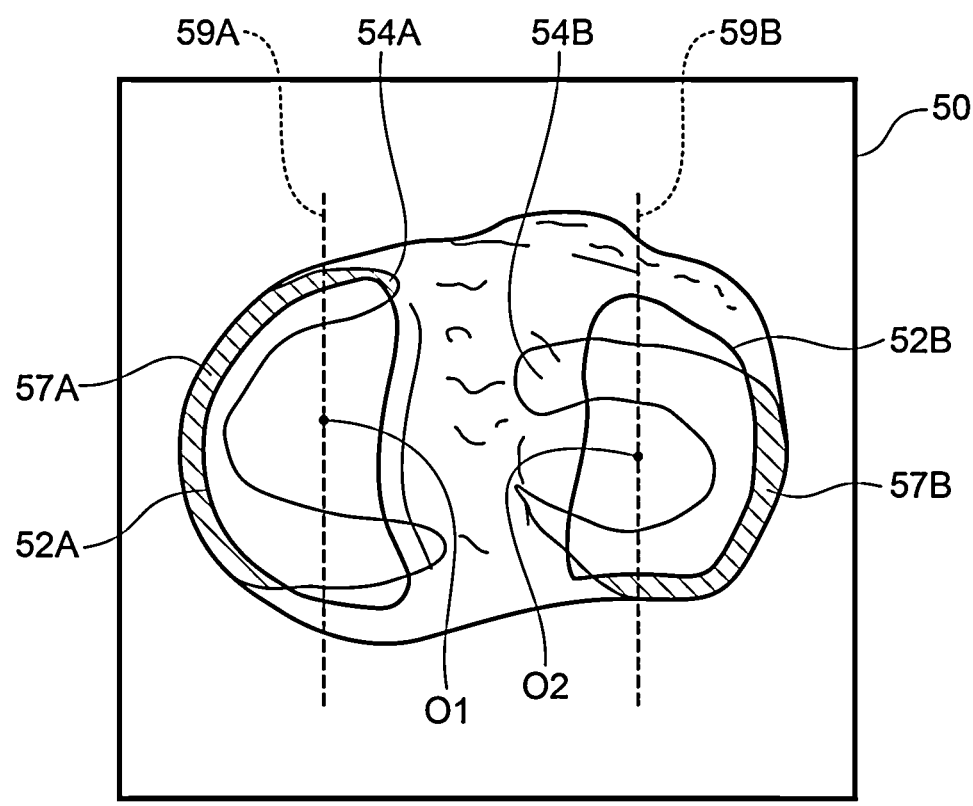
FIG. 21 is a diagram for describing deriving of quantitative values of the menisci that are out of the regions of interest.

On the other hand, the menisci 34 may move out of the region of interest due to a load or impact. The term "out of the region of interest" means a more medial area for the medial region of interest 52A, while the term "out of the region of interest" means a more lateral area for the lateral region of interest 52B. Thus, in the present embodiment, the quantification unit 24 may derive quantitative values of the menisci 34 that are out of the regions of interest. FIG. 21 is a diagram for describing deriving of the quantitative values of the menisci 34 that are out of the regions of interest. As illustrated in FIG. 21, the quantification unit 24 sets the reference points O1 and O2, which are substantially the same as those in FIG. 18, in the projection image 50. Then, as for the medial meniscus region 54A, the quantification unit 24 determines an out-of-region-of-interest meniscus region 57A that sticks out to the medial side of the knee from the region of interest 52A on the basis of a line 59A perpendicular to the reference point O1 in the projection image 50. In addition, as for the lateral meniscus region 54B, the quantification unit 24 determines an out-of-region-of-interest meniscus region 57B that sticks out to the lateral side of the knee from the region of interest 52B on the basis of a line 59B perpendicular to the reference point O2 in the projection image 50. The out-of-region-of-interest meniscus regions 57A and 57B are hatched in FIG. 21. Then, the quantification unit 24 derives the quantitative values of the menisci 34 in the out-of-region-of-interest meniscus regions 57A and 57B. As the quantitative values, the areas, the volumes, and the thicknesses of the out-of-region-of-interest meniscus regions 57A and 57B can be used. The thicknesses may be representative values of the thicknesses of the menisci 34 in the out-of-region-of-interest meniscus regions 57A and 57B or may be the thicknesses of the menisci 34 at pixel positions of the out-of-region-of-interest meniscus regions 57A and 57B on the projection image 50.

Figure 22:
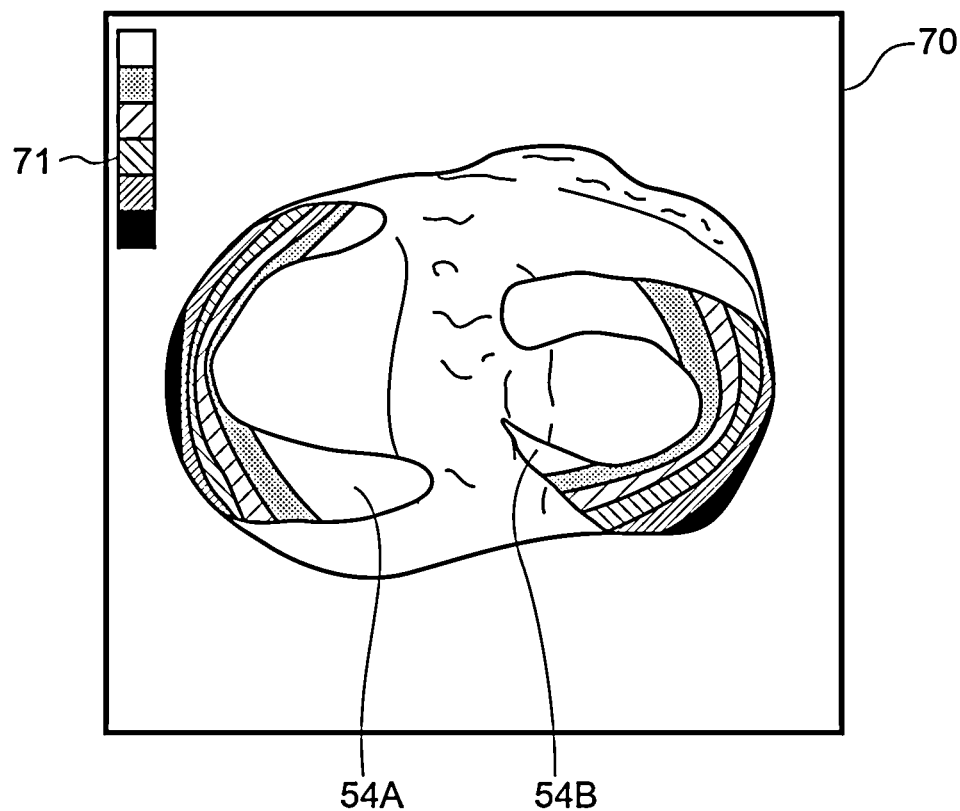
FIG. 22 is a diagram illustrating a thickness map of the menisci.

If the thicknesses of the menisci 34 at pixel positions of the projection image 50 are derived as the quantitative values, the quantification unit 24 may derive a thickness map of the thicknesses of the menisci 34 as the quantitative values. FIG. 22 is a diagram illustrating a thickness map of the menisci. As illustrated in FIG. 22, in a thickness map 70, a distribution of the thicknesses of the meniscus regions 54A and 54B in the projection image is illustrated by 6-level colors. In the thickness map 70, the darker the color is, the thicker the meniscus regions 54A and 54B are. Note that the color differences are represented by hatching differences in FIG. 22. In addition, the thickness map 70 includes a reference 71 indicating a relationship between the color and the thickness. By referring to the reference 71, it is possible to visually recognize the distribution of the thicknesses of the meniscus regions 54A and 54B in the thickness map 70 with ease.

Note that the derived quantitative values are transmitted to the image storage server 3 and stored therein in association with the three-dimensional image V0 together with information such as the patient's name, an imaging date, the positions of the region of interest 52A and the region of interest 52B, and the projection image 50. In addition to the imaging date, an imaging time may also be stored on the image storage server 3.

The display control unit 25 causes the display 6 to display the projection image 50 together with the quantitative values.

Figure 23:
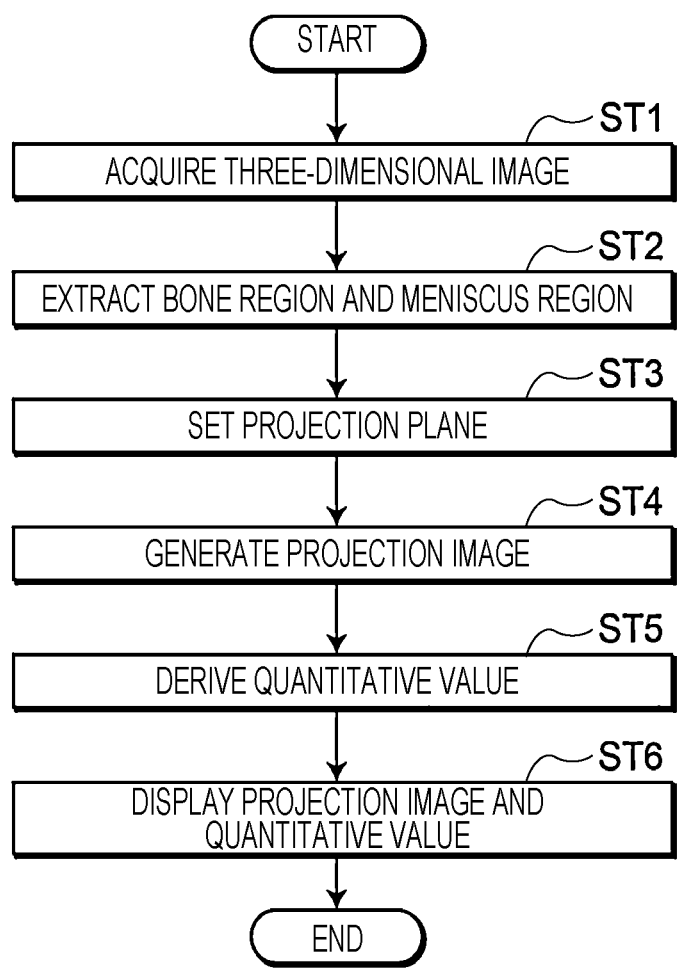
FIG. 23 is a flowchart illustrating a process performed in the present embodiment.

Next, a process performed in the present embodiment will be described. FIG. 23 is a flowchart illustrating the process performed in the present embodiment. First, the image acquisition unit 21 acquires the three-dimensional image V0 (step ST1) and extracts a bone region and a meniscus region from the three-dimensional image V0 (step ST2). Note that, as described above, the image acquisition unit 21 may also extract a cartilage region. Subsequently, the plane setting unit 22 sets a plane that approximates a joint surface of a joint of the tibia 31 as the projection plane 46 for generating a projection image by projecting the three-dimensional image V0 (step ST3).

Subsequently, the projection unit 23 generates the projection image 50 by projecting a meniscus 34 at the joint in the three-dimensional image V0 in the direction orthogonal to the projection plane 46 (step ST4). Then, the quantification unit 24 derives a quantitative value of the meniscus 34 in the projection image 50 (step ST5). Furthermore, the display control unit 25 causes the display 6 to display the projection image 50 and the quantitative value (step ST6), and the process ends.

In the above manner, in the present embodiment, the plane that approximates the joint surface of the joint is set as the projection plane 46 for generating the projection image by projecting the three-dimensional image V0. This can prevent a lost portion of the meniscus from being projected as if the meniscus is present, in particular, as for a joint surface of a comparatively flat joint, such as the tibia 31. Thus, according to the present embodiment, the projection plane for generating the projection image 50 of the meniscus can be set appropriately from the three-dimensional image V0 including the joint.

Figure 24:
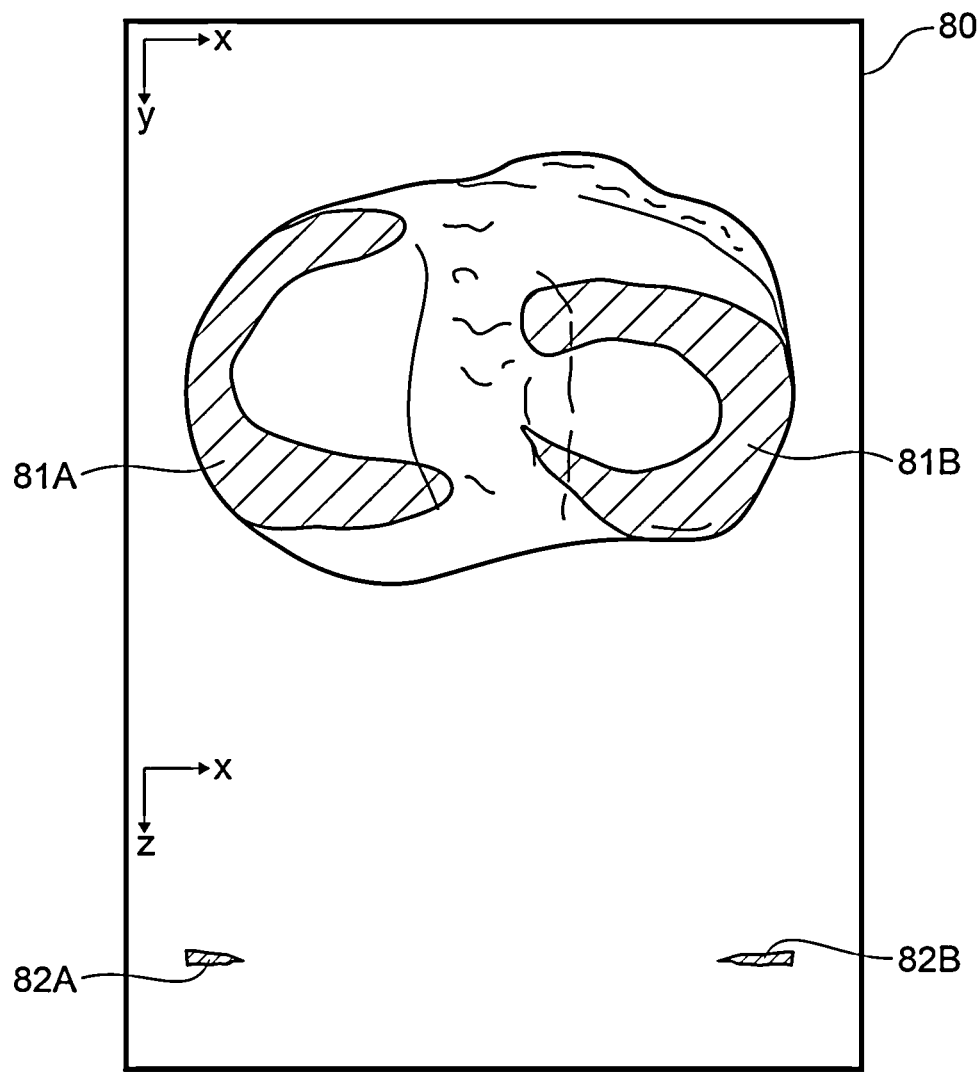
FIG. 24 is a diagram for describing generation of a three-dimensional projection image.
Figure 25:
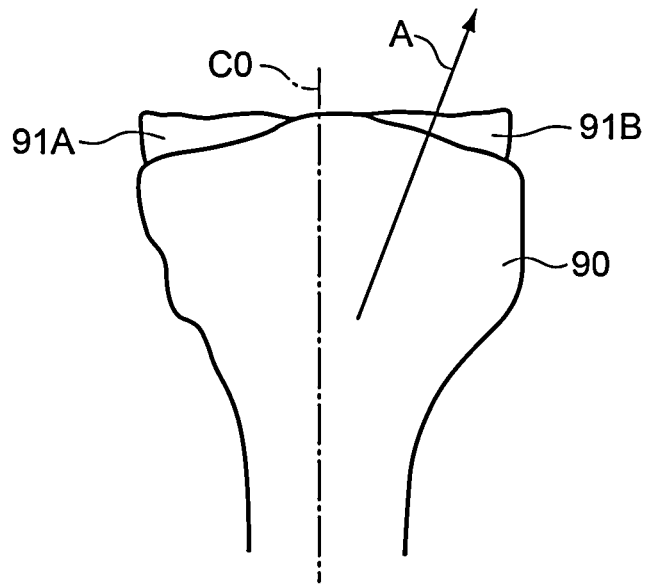
FIG. 25 is a diagram for describing generation of a projection image of a meniscus.
Figure 26:
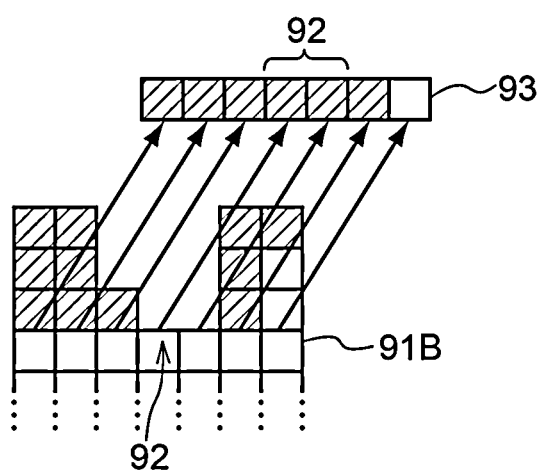
FIG. 26 is a diagram for describing generation of the projection image of the meniscus.

Note that the projection unit 23 generates the two-dimensional projection image 50 in the above embodiment, but the projection unit 23 may generate a three-dimensional projection image. FIG. 24 is a diagram illustrating a three-dimensional projection image. As illustrated in FIG. 24, a projection image 80 includes, as in the above embodiment, meniscus regions 81A and 81B of the tibia 31 and cross-sectional views 82A and 82B illustrating the thicknesses of the meniscus regions 81A and 81B. Note that the positions of cross sections in the cross-sectional views 82A and 82B may be changeable. For example, the positions of cross sections may be changeable radially from the centers that are the reference points O1 and O2 in FIG. 18. Also for the three-dimensional projection image 80 generated in this manner, the quantitative values can be derived and displayed in the above-described manner.

In addition, in the above embodiment, when generating projection images from three-dimensional images V0 of a plurality of different test subjects, the same projection plane may be set. In this case, the projection plane for further generating projection images is preferably the same in the three-dimensional images V0 of the plurality of different test subjects. Thus, states of the menisci of the test subjects can be compared with each other with ease.

Furthermore, in the above embodiment, the areas, volumes, thicknesses, and representative values of the thicknesses of the menisci 34, the coverages of the in-region-of-interest meniscus regions 55A and 55B, and the areas, volumes, thicknesses, or the like of the out-of-region-of-interest meniscus regions 57A and 57B are derived as the quantitative values. However, any one or any combination of these quantitative values may also be derived.

In addition, the projection plane is set by using both the joint surface regions 43 and 44 on the joint surface of the medial condyle and the joint surface of the lateral condyle in the above embodiment, but the present disclosure is not limited to this. The projection plane may be set by using only the joint surface region 43 on the joint surface of the medial condyle. In this case, by using the set projection plane, the projection image of the joint surface region 43 on the joint surface of the medial condyle may be generated. On the other hand, the projection plane may be set by using only the joint surface region 44 on the joint surface of the lateral condyle. In this case, by using the set projection plane, the projection image of the joint surface region 44 on the joint surface of the lateral condyle may be generated.

Furthermore, the process of setting a new projection plane by excluding a voxel is performed repeatedly in the above embodiment, but the present disclosure is not limited to this. On the initially set projection plane 45, voxels whose distance corresponds to the predetermined ratio from the maximum among distances from the voxels in the joint surface regions 43 and 44 to the projection plane 45 may be excluded to set a final projection plane. In this case, the predetermined ratio may be the same as, or larger than, that in a case where the process of setting a new projection plane is performed a plurality of times by excluding a voxel. For example, the predetermined ratio may be 20%.

In addition, in the above embodiment, for example, as a hardware configuration of a processing unit that executes various processes, such as the image acquisition unit 21, the plane setting unit 22, the projection unit 23, the quantification unit 24, and the display control unit 25, various processors below can be used. The various processors include, in addition to a CPU, which is a general-purpose processor that functions as various processing units by executing software (programs) as described above, a programmable logic device (PLD), which is a processor in which the circuit configuration is changeable after manufacture, such as an FPGA (Field Programmable Gate Array), a dedicated electric circuit, which is a processor having a circuit configuration that is specially designed to execute specific processing, such as an ASIC (Application Specific Integrated Circuit), and the like.

One processing unit may be constituted by one of these various processors or may be constituted by two or more processors of the same type or different types in combination (e.g., a combination of a plurality of FPGAs or a combination of a CPU and an FPGA). In addition, a plurality of processing units may be constituted by one processor.

As a first example for constituting a plurality of processing units by one processor, one processor may be constituted by a combination of one or more CPUs and software, and this processor may function as a plurality of processing units, as typified by a computer such as a client or a server. As a second example, a processor may be used that implements the functions of the entire system including a plurality of processing units with one IC (Integrated Circuit) chip, as typified by a system on chip (SoC) or the like. In this manner, various processing units are constituted by one or more of the above various processors in terms of hardware configuration.

More specifically, the hardware configuration of these various processors may be electric circuitry constituted by combining circuit elements such as semiconductor elements.

REFERENCE SIGNS LIST 1 meniscus projection plane setting apparatus
2 three-dimensional imaging apparatus
3 image storage server
4 network
6 display
7 input device
11 CPU
12 memory
13 storage
14 communication I/F
21 image acquisition unit
22 plane setting unit
23 projection unit
24 quantification unit
25 display control unit
30 femur
31 tibia
32, 33 cartilage
34 meniscus
40 three-dimensional region
40A top surface
41 side
42 region between condyles
43, 44 joint surface region
45, 45A, 45B, 46 projection plane
47 direction orthogonal to projection plane
48 line connecting centers of gravity
49 Akagi line
50 projection image
51A, 51B, 56A, 56B cartilage region
52A, 52B, 56A, 56B region of interest
54A, 54B, 81A, 81B meniscus region
54A-F, 54B-F front section
54A-M, 54B-M middle section
54A-B, 54B-B back section
55A, 55B in-region-of-interest meniscus region
57A, 57B out-of-region-of-interest meniscus region
59A, 59B line
60, 65 display screen
61, 62, 68, 69 coverage
66 previous projection image
67 current projection image
70 thickness map
71 reference
80 projection image
82A, 82B cross-sectional view
90 tibia
91A, 91B meniscus
92 lost portion
93 projection image
C0 central axis
G1, G2 center of gravity
L1-1, L1-2 L1-$n$, L31, L32, L33, L41, L42, L43 reference line
P1 voxel
O1, O2 reference point
V0, V1, V2 three-dimensional image

What is claimed is:

1. A meniscus projection plane setting apparatus comprising
at least one processor configured to:
acquire a three-dimensional image of a knee joint;
set a plane that approximates a joint surface of the knee joint as a projection plane for generating a projection image by projecting a meniscus at the knee joint included in the three-dimensional image; and
exclude, from among pixel positions on the joint surface, a pixel position whose distance from the projection plane is greater than or equal to a predetermined threshold and set a new projection plane.

2. The meniscus projection plane setting apparatus according to claim 1, wherein the distance from the projection plane of the excluded pixel position corresponds to a predetermined ratio from the maximum among distances from the pixels on the joint surface to the projection plane.

3. The meniscus projection plane setting apparatus according to claim 2, wherein the processor is configured to set the projection plane by repeating excluding of the pixel position and setting of the new projection plane a plurality of times.

4. The meniscus projection plane setting apparatus according to claim 1, wherein the processor is configured to set the plane that approximates the joint surface by a least squares method.

5. The meniscus projection plane setting apparatus according to claim 1, wherein the knee joint is a tibial joint.

6. The meniscus projection plane setting apparatus according to claim 5, wherein the processor is configured to extract, as a joint surface region, a region excluding a region between condyles from an image in which a joint surface of the tibia is viewed in a predetermined direction and set, as the projection plane, a plane that approximates the joint surface included in the joint surface region.

7. The meniscus projection plane setting apparatus according to claim 5, wherein the processor is configured to generate the projection image by further projecting the meniscus at the knee joint in the three-dimensional image in a direction orthogonal to the projection plane such that a line connecting a center of gravity of a joint surface of a medial condyle of the tibia and a center of gravity of a joint surface of a lateral condyle of the tibia is oriented in a predetermined direction.

8. The meniscus projection plane setting apparatus according to claim 5, wherein the processor is configured to generate the projection image by further projecting the meniscus at the knee joint in the three-dimensional image in a direction orthogonal to the projection plane such that an Akagi line at the tibia when viewed in a direction perpendicular to the projection plane is oriented in a predetermined direction.

9. The meniscus projection plane setting apparatus according to claim 1, wherein the processor is configured to generate the projection image by further projecting the meniscus at the knee joint in the three-dimensional image in a direction orthogonal to the projection plane.

10. The meniscus projection plane setting apparatus according to claim 9, wherein the processor is configured to further cause a display to display the projection image.

11. The meniscus projection plane setting apparatus according to claim 9, wherein the processor is configured to set, in a case where there is another projection image generated from another three-dimensional image whose imaging timing is different for a same test subject as a test subject for which the three-dimensional image is acquired, a projection plane, by which the other projection image is generated, as the projection plane for generating the projection image by projecting the three-dimensional image.

12. The meniscus projection plane setting apparatus according to claim 9, wherein the processor is configured to further derive a quantitative value of the meniscus in the projection image.

13. The meniscus projection plane setting apparatus according to claim 12, wherein the processor is configured to divide the meniscus in the projection image into a plurality of regions and derive the quantitative value in each of the regions obtained by dividing.

14. The meniscus projection plane setting apparatus according to claim 12, wherein the processor is configured to derive, as the quantitative value, at least one of an area of the meniscus, a volume of the meniscus, a lost area of the meniscus, a representative value of a thickness of the meniscus, or thicknesses of the meniscus at positions of the projection image.

15. The meniscus projection plane setting apparatus according to claim 14, wherein the processor is configured to generate a thickness map of the meniscus in a case of deriving the thicknesses of the meniscus at the positions of the projection image.

16. The meniscus projection plane setting apparatus according to claim 15, wherein the processor is configured to further cause a display to display the thickness map.

17. The meniscus projection plane setting apparatus according to claim 12, wherein the processor is configured to derive the quantitative value of the meniscus within or out of a region of interest at the knee joint in the three-dimensional image in the projection image.

18. The meniscus projection plane setting apparatus according to claim 17, wherein the processor is configured to derive, as the quantitative value, a coverage of the meniscus in the region of interest.

19. The meniscus projection plane setting apparatus according to claim 17, wherein the processor is configured to derive, as the quantitative value, at least one of a volume of the meniscus out of the region of interest, an area of the meniscus out of the region of interest, or a thickness of the meniscus out of the region of interest.

20. The meniscus projection plane setting apparatus according to claim 17, wherein the region of interest is a region where a subchondral bone region or a cartilage is supposed to be present at the knee joint.

21. The meniscus projection plane setting apparatus according to claim 17, wherein the processor is configured to set, in a case where there is a derived result of another quantitative value derived from another three-dimensional image whose imaging timing is different for a same test subject as a test subject for which the three-dimensional image is acquired, the region of interest at a same position as a position of the region of interest in deriving the other quantitative value.

22. A meniscus projection plane setting method comprising:
    acquiring a three-dimensional image of a knee joint;
    setting a plane that approximates a joint surface of the knee joint as a projection plane for generating a projection image by projecting a meniscus at the knee joint included in the three-dimensional image; and
    excluding, from among pixel positions on the joint surface, a pixel position whose distance from the projection plane is greater than or equal to a predetermined threshold and setting a new projection plane.

23. A non-transitory computer readable recording medium storing a meniscus projection plane setting program for causing a computer to execute:
    acquiring a three-dimensional image of a knee joint;
    setting a plane that approximates a joint surface of the knee joint as a projection plane for generating a projection image by projecting a meniscus at the knee joint included in the three-dimensional image; and
    excluding, from among pixel positions on the joint surface, a pixel position whose distance from the projection plane is greater than or equal to a predetermined threshold and setting a new projection plane.

* * * * *